United States Patent
Aalto et al.

(10) Patent No.: US 11,274,300 B2
(45) Date of Patent: Mar. 15, 2022

(54) OLIGONUCLEOTIDE COMPLEXES FOR USE IN RNA EDITING

(71) Applicant: ProQR Therapeutics II B.V., Leiden (NL)

(72) Inventors: Antti Aalto, Leiden (NL); Janne Juha Turunen, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 173 days.

(21) Appl. No.: 16/479,101

(22) PCT Filed: Jan. 18, 2018

(86) PCT No.: PCT/EP2018/051202
§ 371 (c)(1),
(2) Date: Jul. 18, 2019

(87) PCT Pub. No.: WO2018/134301
PCT Pub. Date: Jul. 26, 2018

(65) Prior Publication Data
US 2019/0352641 A1   Nov. 21, 2019

(30) Foreign Application Priority Data

Jan. 19, 2017   (GB) .................................... 1700939
May 10, 2017   (GB) .................................... 1707511

(51) Int. Cl.
*C12N 15/11*   (2006.01)
(52) U.S. Cl.
CPC ........ *C12N 15/111* (2013.01); *C12N 2310/11* (2013.01); *C12N 2310/315* (2013.01); *C12N 2310/346* (2013.01); *C12Y 305/04* (2013.01)

(58) Field of Classification Search
None
See application file for complete search history.

(56) References Cited

U.S. PATENT DOCUMENTS

| | | | |
|---|---|---|---|
| 8,372,816 | B2 | 2/2013 | Brown |
| 9,650,627 | B1 | 5/2017 | Rosenthal et al. |
| 9,732,347 | B2 | 8/2017 | Brown et al. |
| 10,676,737 | B2 | 6/2020 | Klein et al. |
| 10,941,402 | B2 | 3/2021 | Turunen et al. |
| 10,988,763 | B2 | 4/2021 | Turunen et al. |
| 2014/0228556 | A1 | 8/2014 | Fukuda et al. |
| 2014/0357856 | A1 | 12/2014 | Monia et al. |
| 2017/0355985 | A1 | 12/2017 | Dellinger et al. |
| 2019/0093098 | A1 | 3/2019 | Stafforst et al. |
| 2019/0218552 | A1 | 7/2019 | Turunen et al. |
| 2019/0330622 | A1 | 10/2019 | Turunen et al. |
| 2019/0352641 | A1 | 11/2019 | Aalto et al. |
| 2020/0199586 | A1 | 6/2020 | Klein et al. |
| 2021/0079393 | A1 | 3/2021 | Boudet et al. |

FOREIGN PATENT DOCUMENTS

| | | |
|---|---|---|
| DE | 102015012522 B3 | 6/2016 |
| EP | 3323890 A1 | 5/2018 |
| EP | 3353299 B1 | 3/2020 |
| GB | 1610923 | 8/2016 |
| JP | 2008194035 A | 8/2008 |
| WO | WO-2000/066604 A2 | 11/2000 |
| WO | WO-2004/091515 A2 | 10/2004 |
| WO | WO-2005/094370 A2 | 10/2005 |
| WO | WO-2010/064146 A2 | 6/2010 |
| WO | WO-2011/072082 A2 | 6/2011 |
| WO | WO-2011085271 A2 | 7/2011 |
| WO | WO-2011/119887 A1 | 9/2011 |
| WO | WO-2012/138487 A2 | 10/2012 |
| WO | WO-2013/075035 A1 | 5/2013 |
| WO | WO-2014/011053 A1 | 1/2014 |
| WO | WO-2014/012081 A2 | 1/2014 |
| WO | WO-2014/203518 A1 | 12/2014 |
| WO | WO-2016/062886 A1 | 4/2016 |
| WO | WO-2016/079181 A1 | 5/2016 |
| WO | WO-2016/089433 A1 | 6/2016 |
| WO | WO-2016/094845 A2 | 6/2016 |
| WO | WO-2016/096938 A1 | 6/2016 |
| WO | WO-2016/097212 A1 | 6/2016 |
| WO | WO-2017/015555 A1 | 1/2017 |
| WO | WO-2017/050306 A1 | 3/2017 |
| WO | WO-2017/053431 A2 | 3/2017 |
| WO | WO-2017/192664 A1 | 11/2017 |

(Continued)

OTHER PUBLICATIONS

Angus Lamond et al. (1993) "Antisense oligonucleotides made of 2'-O-alkylRNA: their properties and applications in RNA biochemistry," FEBS Lett., 325(1-2):123-7.
Aruscavage et al. (2000) "A phylogenetic analysis reveals an unusual sequence conservation within introns involved in RNA editing," RNA, 6(2):257-69.
Bajas et al. (2017) RNA Biology, 14,(9):1223-1231.
Boots et al. (2017) Neurology, 88(22):2098-2106.
Brown et al. (1994) J. Biol. Chem., 269(43): 26801-26805.
Case et al. (2005) J. Comput. Chem., (16): 1668-1688.
Chen et al. (2019) "RNA-Guided Adenosine Deaminases: Advances and Challenges for Therapeutic RNA Editing," Biochemistry, 58: 1947-1957.
Dawson, et al. (2004) J. Biol. Chem., 279(6): 4941-4951.
Diaz et al. (2004) J. Mol. Biol., 342: 971-985.
Grunewald et al. (2014) "Does uncoupling protein 2 expression qualify as marker of disease status in LRRK2-associated Parkinson's disease," Antioxid. Redox Signal., 20(13):1955-60.

(Continued)

Primary Examiner — Tracy Vivlemore
(74) Attorney, Agent, or Firm — Goodwin Procter LLP

(57) ABSTRACT

The invention relates to double stranded oligonucleotide complexes comprising an antisense oligonucleotide (AON) and a complementary sense oligonucleotide (SON), for use in the deamination of a target adenosine in a sense target RNA sequence in a cell by an ADAR enzyme, wherein at least the nucleotide in the AON that is directly opposite the target adenosine in the target RNA sequence does not have a 2'-O-alkyl modification and the SON comprises nucleotides that are at least complementary to all nucleotides in the AON that do not have a 2'-O-alkyl modification. The invention further relates to methods of RNA editing using the AON/SON complexes of the invention.

20 Claims, 9 Drawing Sheets

Specification includes a Sequence Listing.

(56) References Cited

FOREIGN PATENT DOCUMENTS

| | | | |
|---|---|---|---|
| WO | WO-2017/220751 A1 | 12/2017 | |
| WO | WO-2018/041973 A1 | 3/2018 | |
| WO | WO-2018/126176 A1 | 7/2018 | |
| WO | WO-2018/134301 A1 | 7/2018 | |
| WO | WO-2019/005884 A1 | 1/2019 | |
| WO | WO-2019/158475 A1 | 8/2019 | |
| WO | WO-2019/191232 A2 | 10/2019 | |
| WO | WO-2019/219581 A1 | 11/2019 | |
| WO | WO-2020/252376 A1 | 12/2020 | |

OTHER PUBLICATIONS

Hallegger et al. (2006) "RNA aptamers binding the double-stranded RNA-binding domain," RNA., 12(11):1993-2004.
International Search Report for PCT/EP2015/080347, dated Apr. 1, 2016 (5 pages).
International Search Report for PCT/EP2017/065467, dated Sep. 15, 2017 (5 pages).
International Search Report for PCT/EP2017/071912, dated Dec. 15, 2017 (5 pages).
International Search Report for PCT/EP2018/051202, dated Mar. 19, 2018 (6 pages).
International Search Report for PCT/EP2019/053291, dated Jun. 6, 2019 (6 pages).
International Search Report for PCT/EP2019/062163, dated Jul. 31, 2019 (6 pages).
International Search Report for PCT/US2020/037580 dated Oct. 2, 2020 (5 pages).
Iwamoto, et al. (2017) Nature Biotech., 35(9): 845-851.
Juliano (2016) "The delivery of therapeutic oligonucleotides," Nucleic Acid Research, 44: 6518-6548.
Kumar et al. Microbiology and Molecular Biology Reviews, vol. 62, p. 1415-1434 (Year: 1998).
Lancaster et al. (2014) "Organogenesis in a dish: modeling development and disease using organoid technologies," Science, 345(6194):1247125.
Masliah et al. (2013) "RNA recognition by double-stranded RNA binding domains: a matter of shape and sequence," Cell Mol. Life Sci., 70(11):1875-95.
Matthews et al. (2016) "Structures of Human ADAR2 Bound to dsRNA Reveal Base-Flipping Mechanism and Basis for Site Selectivity," Nat. Struct. Mol. Biol., 23(5): 426-433.
Mei et al. Trends in Pharmacological Sciences vol. 41, pp. 475-486 (Year: 2020).
Merkle et al. (2019) "Precise RNA editing by recruiting endogenous ADARs with antisense oligonucleotides," Nature Biotechnology, 37: 133-138.
Mizrahi et al. ACS Chem. Bio. supporting information, pp. 1-4 (Year: 2013).
Mizrahi et al. ACS Chem. Biol. 8, 832-839 (Year: 2013).
Montiel-Gonzalez et al. (2013) "Correction of mutations within the cystic fibrosis transmembrane conductance regulator by site-directed RNA editing," Proc. Natl Acad. Sci. USA, 110(45):18285-90.
Montiel-Gonzalez et al. (2016) "An Efficient System for Selectively Altering Genetic Information Within mRNAs," Nucleic Acid Research, 44(21): e157 (12 pages).
Montiel-Gonzalez et al. (2019) "Current strategies for Site-Directed RNA Editing using ADARs," Methods, 156: 16-24.
Nelwan, M. Journal of Advances in Biology & Biotechnology 16(3): 1-12 (Year: 2017).
Papkovskaia et al. (2012) "G2019S leucine-rich repeat kinase 2 causes uncoupling protein-mediated mitochondrial depolarization," Hum. Mol. Genet., 21(19):4201-13.
Rutten et al. Brain 139: 1123-1135 (Year: 2016).
Saccomanno et al. (1999) "A minor fraction of basic fibroblast growth factor mRNA is deaminated in Xenopus stage VI and matured oocytes," RNA, 5: 39-48.
Sala et al. (2009) "Tissue-engineered small intestine and stomach form from autologous tissue in a preclinical large animal model," J Surg. Res., 156(2):205-12.
Sato et al. (2011) "Long-term expansion of epithelial organoids from human colon, adenoma, adenocarcinoma, and Barrett's epithelium," Gastroenterology, 141 (5):1762-72.
Schade et al. (1999) "A 6 bp Z-DNA hairpin binds two Zα domains from the human RNA editing enzyme ADAR1," FEBS Lett., 458(1):27-31.
Schneider et al. (2014) "Optimal guide RNAs 1-29 for re-directing deaminase activity of hADAR1 and hADAR2 in trans," Nucleic Acids Res., 42(10):e87-e87.
Schneider et al. (2014) "Supporting Information: Optimal GuideRNAs for Re-directing Deaminase Activity of hADAR1 and hADAR2 in Trans," URL: http://nar.oxfordjournals.org/content/suppl/2014/04/05/gku272.DC1/nar-03496-met-g-2013-File007.pdf (15 pages).
Score result to Fukuoka University 2015. (Year: 2015).
Score result to Lavanon et al. WO2005-087949. (Year: 2005).
Score result to Masatora et al. 2015. (Year: 2015).
Search Report for GB1700939.0, dated Oct. 1, 2017 (2 pages).
Sharma et al. (2015) "Oligonucleotide Therapeutics: Chemistry, Delivery and Clinical Progress," Future Med. Chem., 7(16): 2221-2422.
Singleton et al. (1999) Structure, 7(3): 237-244.
Smith et al. (2016) "Fibroblast Biomarkers of Sporadic Parkinson's Disease and LRRK2 Kinase Inhibition," Mol. Neurobiol., 53(8):5161-77.
Stafforst et al. (2012) "An RNA-deaminase Conjugate Selectively Repairs Point Mutations," Angewandte Chemie Int. Ed., 51 (44): 11166-11169.
Stafforst et al. (2012) "Supporting Information: An RNA-deaminase Conjugate Selectively Repairs Point Mutations," URL: PQR-013_https://onlinelibrary.wiley.com/action/downloadSupplement?doi=10.1002%2Fanie.201206489&file=anie_201206489_sm_miscellaneous_information.pdf (23 pages).
Stefl et al. (2006) "Structure and Specific RNA Binding of ADAR2 Double-Stranded RNA Binding Motifs," Structure 14(2): 345-355.
Tian et al. (2004) "The double-stranded-RNA-binding motif: interference and much more," Nat. Rev. Mol. Cell Biol., 5(12):1013-23.
Tian et al. (2011) "A Structural Determinant Required for RNA Editing," Nucleic Acids Res. 39(13): 5669-5681.
Turunen, "Axiomer Technology. Therapeutic oligonucleotides for directing site-specific A-to-I editing by endogenous ADAR enzymes," Sep. 25, 2017 (Retrieved from https://www.proqr.com/wp-content/uploads/downloads/2017/11/Axiomer%20technology%20QTS%20170921.pdf) (22 pages).
UKIPO Search Report for GB1808146.3, dated Jan. 30, 2019 (5 pages).
Vogel et al. (2014) "Improving site-directed RNA editing in vitro and in cell culture by chemical modification of the guideRNA," Angew Chem Int Ed Engl., 53(24):6267-71.
Vogel et al. (2014) ChemMedChem, 9(20):2021-2025.
Woolf et al. (1995) "Toward the therapeutic editing of mutated RNA sequences," Proc. Natl. Acad. Sci. USA, 92(18):8298-8302.
Written Opinion for PCT/EP2015/080347, dated Apr. 1, 2016 (5 pages).
Written Opinion for PCT/EP2017/065467, dated Sep. 15, 2017 (5 pages).
Written Opinion for PCT/EP2017/071912, dated Dec. 15, 2017 (5 pages).
Written Opinion for PCT/EP2018/051202, dated Mar. 19, 2018 (7 pages).
Written Opinion for PCT/EP2019/053291, dated Jun. 6, 2019 (5 pages).
Written Opinion for PCT/EP2019/062163, dated Jul. 31, 2019 (6 pages).
Written Opinion for PCT/US2020/037580, dated Oct. 2, 2020 (7 pages).
Yang et al. (2006) "Artificially expanded genetic information system: a new base pair with an alternative hydrogen bonding pattern," Nucleic Acid Research, 34(21): 6095-6101.
Zangemeister-Wittke et al. (2000) Clinical Cancer Research, 6(6):2547-2555.

(56) References Cited

OTHER PUBLICATIONS

Zheng et al. (2017) Nucleic Acids Research, 45(6):3369-3377.
Zhou et al. (2009) Proteins, 76(1): 151-163.
Anonymous (2008) The Glen Report, 20(2): 1-4.
Desterro et al., "Dynamic association of RNA-editing enzymes with the nucleolus" *J Cell Sci.*, May 2003; 116(Pt9):1805-18.
Document D8 cited in Opposition of European Patent No. 3234134 "Examples of pairs of known RNA sequences in which one of the pairs meets the requirements of the Patent."
Fukuda et al., "Construction of a guide-RNA for site-directed RNA mutagenesis utilising intracellular A-to-I RNA editing" *Scientific Reports*, Feb. 2017.
Garncarz et al., "A high throughput screen to identify enhancers of ADAR-mediated RNA-editing" *RNA Biology*, Feb. 2013; 10(2):192-204.
Herrmann et al. (2002) J.Mol. Biol., 319: 209-227.
Higuchi et al., (1993); "RNA Editing of AMPA Receptor Subunit GluR-8:A Base-Paired Intron-Exon Structure Determines Position and Efficiency" *Cell* 75:1361-1370.
International Search Report for PCT/EP2020/053283, dated Jul. 17, 2020 (8 pages).
Juliano et al. (2012) "Cellular Uptake and Intracellular Trafficking of Antisense and siRNA Oligonucleotides," Bioconjug. Chem., 23(2): 147-157.
Kazuko Nishikura (2010), "Functions and Regulation of RNA Editing by ADAR Deaminases", *Annu Rev Biochem.*, 79, pp. 321-349.
Lennox and Behlke, "Chemical modification and design of anti-miRNA oligonucleotides" *Gene Ther.*, Dec. 2011; 18(12): 1111-20.
Lomeli et al., (1994), "Control of kinetic properties of AMPA receptor channels by nuclear RNA editing" *Science*, 266(5191): pp. 1709-1713.
Macbeth et al., (2004), "Evidence for auto-inhibition by the N terminus of hADAR2 and activation bydsRNA binding" *RNA*. (10), pp. 1563-1571.
Matsui et al. (2014) Artificial DNA: PNA & XNA, 5(3): e1146391.
Murayama et al. (2013) Chemistry—A European Journal, 19(42): 14151-14158.
Nose et al., "Short Chain Guide RNA for Site-Directed A-to-I RNA Editing" *Nucleic Acid Therapeutics*, 2020; 00(00): 1-10.
Notice of Opposition by Margaret Dixon Limited, against European Patent No. 3234134, dated Feb. 25, 2021.
Notice of Opposition by Margaret Dixon Limited, against European Patent No. 3507366, dated Jun. 25, 2021.
Pasternak et al. (2011) Organic & Biomolecular Chemistry, 9(10): 3591-3597.
Reider et al., Tertiary structural elements determine the extent and specificity of messenger RNA editing *Nat. Commun.*, Feb. 2013; 4: 2232.
Ryan et al. (2017) Nucleic Acid Research, 46(2): 792-803.
Sheehan et al. (2003) Nucleic Acids Research, 31 (14): 4109-4118.
Statement of Opposition by Strawman Limited, against European Patent No. 3234134, of PROQR Therapeutics II B.V., dated Feb. 25, 2021.
Stefl and Allain, (2005), "A novel RNA pentaloop fold involved in targeting ADAR2", RNA, 11 (5), pp. 592-597.
Document D12 cited in Opposition of European Patent No. 3234134 "Structure of SEQ ID No. 1 of WO2014/011053."
Document D10 cited in Opposition of European Patent No. 3234134 "Structure of the CF4 oligonucleotide of WO2005/094370."
Document D3 cited in Opposition of European Patent No. 3234134 "Structures of the three complementary oligonucleotides disclosed in Figure 2 of Woolf et al. (1995) Proc. Natl. Acad. Sci. USA, 92(18):8298-8302."
Svoboda et al., (2006), "Hairpin RNA: a secondary structure of primary importance", *Cell Mo/ Life Sci*. (7-8), pp. 901-908.
Vaish et al. (2010) Nucleic Acids Research, 39(5): 1823-1832.
Wong et al., (2001), "Substrate recognition by ADAR1 and ADAR2", *RNA*, 7(6), pp. 846-858.
Written Opinion for PCT/EP2020/053283, dated Jul. 17, 2020 (11 pages).

3'-GAUGGACAAGGUACCGGUUGUGAGAGAGUCAUGAAAGAGAGAAUAGAAGAAGUUAC-5'  ADAR59-2 (SEQ ID NO: 1)

5'-CUGUUCCAUGGCCAACACUU-3'  GFP-SON-1 (SEQ ID NO: 2)
5'-GUUCCAUGGCCAACA-3'  GFP-SON-2 (SEQ ID NO: 3)
5'-CUGUUCCAUGGCCAACACUU-3'  GFP-SON-3 (SEQ ID NO: 2)
5'-GUUCCAUGGCCAACA-3'  GFP-SON-4 (SEQ ID NO: 3)
5'-CUGUUCCAUGGCCAACACUU-3'  GFP-SON-5 (SEQ ID NO: 2)
5'-GUUCCAUGGCCAACA-3'  GFP-SON-6 (SEQ ID NO: 3)
5'-CTGTTGGATGGCCAACACTT-3'  GFP-SON-7 (SEQ ID NO: 4)
5'-GTTCCATGGCCAACA-3'  GFP-SON-8 (SEQ ID NO: 5)
5'-CTGTTGGATGGCCAACACTT-3'  GFP-SON-9 (SEQ ID NO: 4)

B

| Target RNA | Name | Sequence w/ modifications |
|---|---|---|
| GFP W57X | GFP-SON-1 | CUGUUCCAUGGCCAACACUU |
| GFP W57X | GFP-SON-2 | GUUCCAUGGCCAACA |
| GFP W57X | GFP-SON-3 | C*U*G*U*U*C*C*A*U*G*G*C*C*A*A*C*A*C*U*U |
| GFP W57X | GFP-SON-4 | G*U*U*C*C*A*U*G*G*C*C*A*A*C*A |
| GFP W57X | GFP-SON-5 | mC*mU*mG*mU*mU*C*C*A*U*G*G*C*C*A*A*C*A*mC*mU*mU |
| GFP W57X | GFP-SON-6 | mG*mU*mU*mC*C*A*U*G*G*C*C*mA*mA*mC*mA |
| GFP W57X | GFP-SON-7 | dCdTdGdTdTdGdGdCdAdTdGdGdCdCdAdAdCdAdCdTdT |
| GFP W57X | GFP-SON-8 | dGdTdTdCdCdAdTdGdGdCdCdAdAdCdA |
| GFP W57X | GFP-SON-9 | pCpTpGpTpTpGpCpApTpGpGpCpCpApApCpApCpTpT |
| GFP W57X | ADAR59-2 | mC*mA*mU*mU*mGmAmAmGmAmAmAmGmAmAmAmGmUmAmCmUmGmAmAmCmUmUmGmCCAmUmGmGCCAmUmUmGmGCCAmUmGmGmAmAmGmUmGmCCAmUmUmGmGCCAmUmGmAmAmGmUmGmGCCAmUmGmCCAmUmGmGCCAmUmGm*mG*mU*mA*mG |

RNA: A, C, G, U
DNA: dA, dC, dG, dT
2'-OMe: mA, mC, mG, mU
PMO: pA, pC, pG, pT
phosphorothioate: *

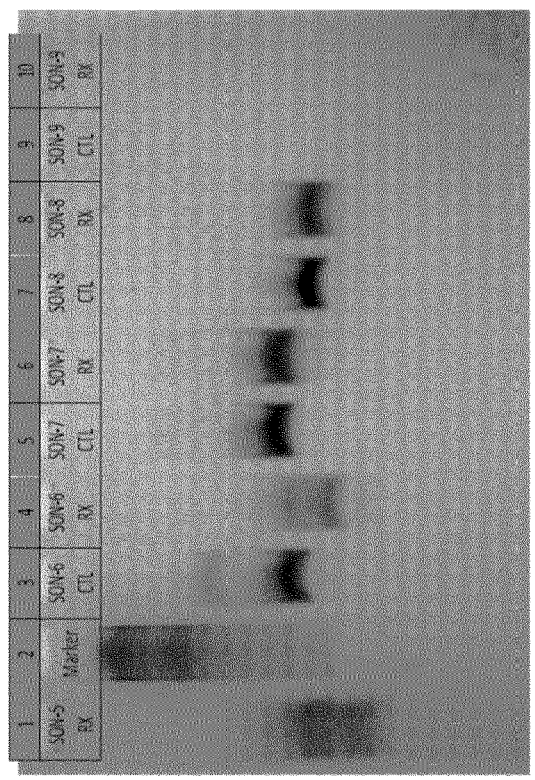
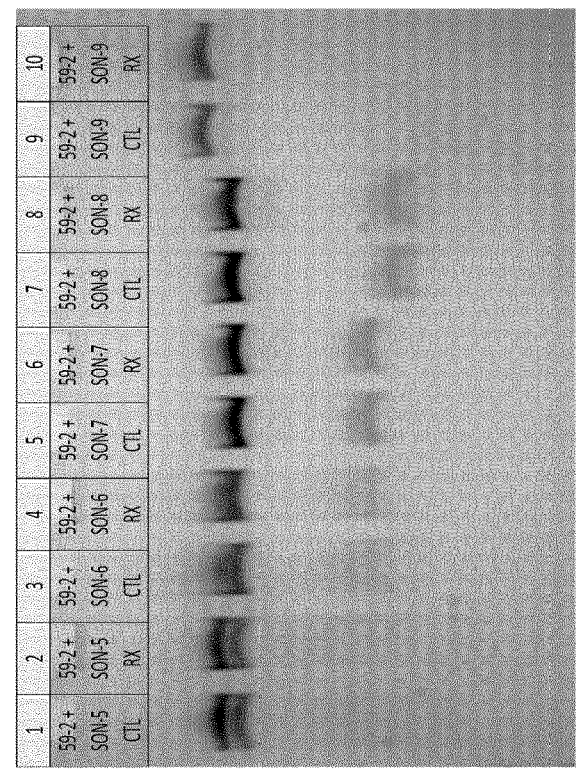
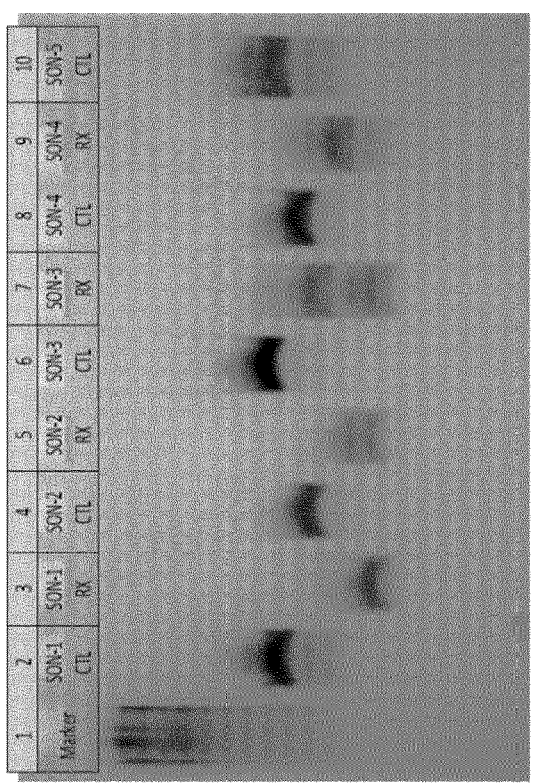
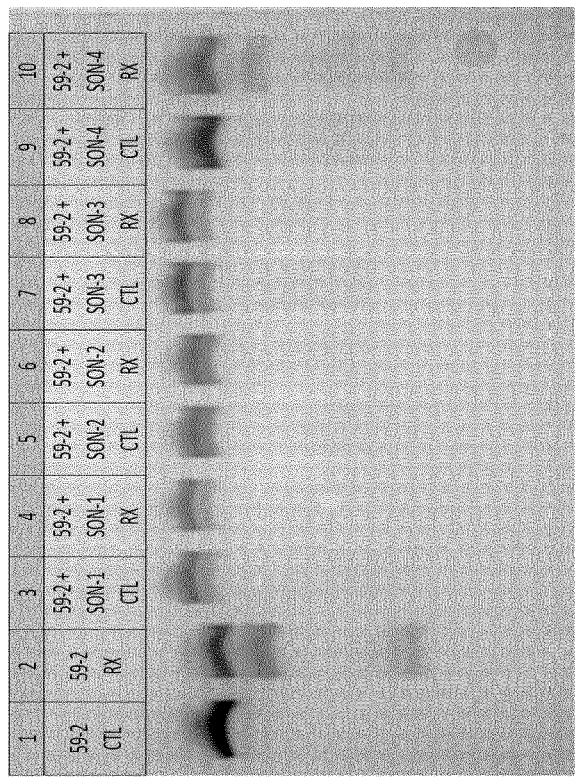
Fig. 2

*Fig. 3*
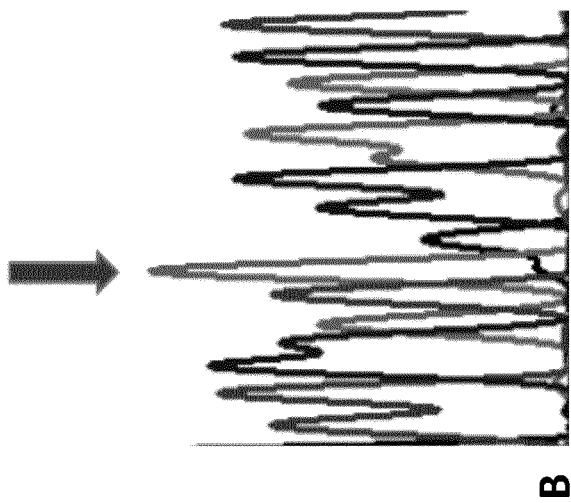
A
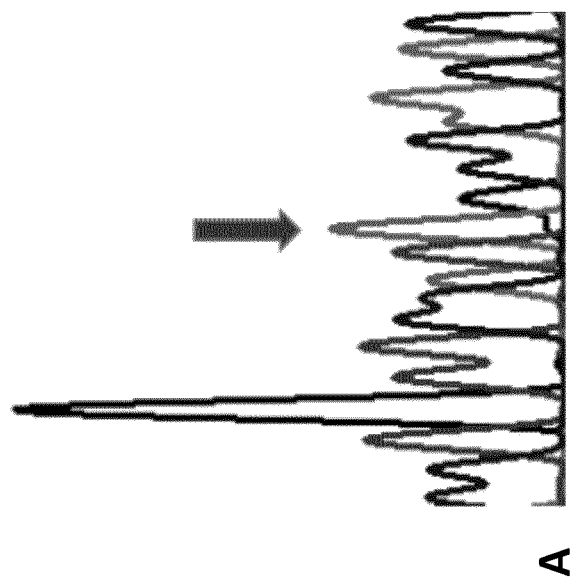
B

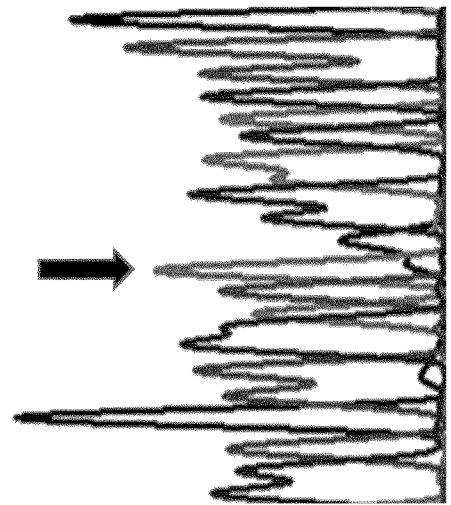
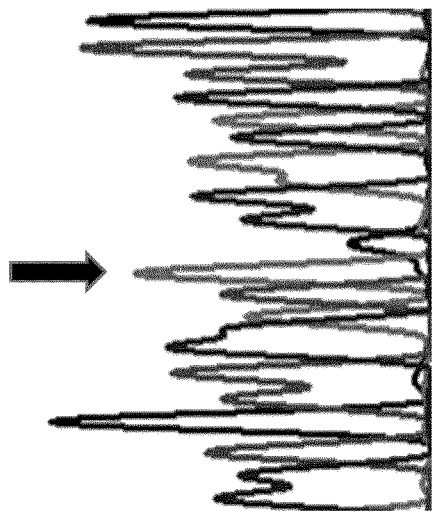
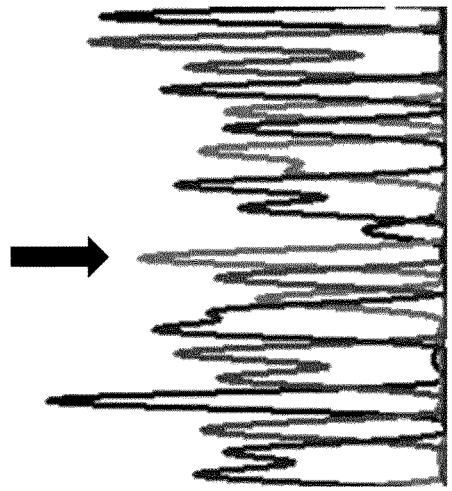
Fig. 4

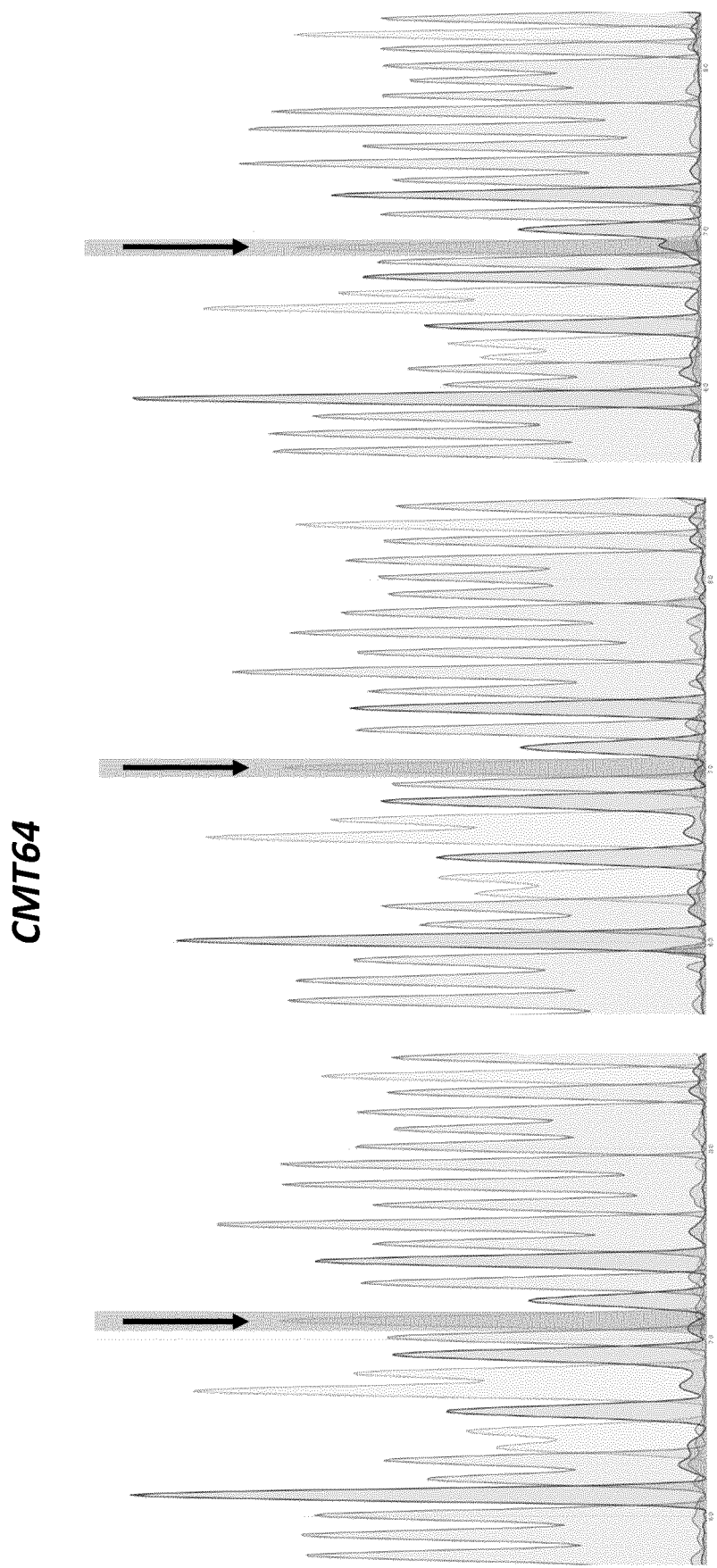

SEQUENCE LISTING

<160> NUMBER OF SEQ ID NOS: 20

<210> SEQ ID NO 1
<211> LENGTH: 53
<212> TYPE: RNA
<213> ORGANISM: Artificial Sequence
<220> FEATURE:
<223> OTHER INFORMATION: ADAR59-2

<400> SEQUENCE: 1
cauugaagaa gauaagagaa aguacugaga aguguuggcc auggaacagg uag            53

<210> SEQ ID NO 2
<211> LENGTH: 20
<212> TYPE: RNA
<213> ORGANISM: Artificial sequence
<220> FEATURE:
<223> OTHER INFORMATION: GFP-SON-1/3/5

<400> SEQUENCE: 2
cuguuccaug gccaacacuu                                                  20

```
<210> SEQ ID NO 3
<211> LENGTH: 15
<212> TYPE: RNA
<213> ORGANISM: Artificial sequence
<220> FEATURE:
<223> OTHER INFORMATION: GFP-SON-2/4/6

<400> SEQUENCE: 3
guuccauggc caaca                                                   15

<210> SEQ ID NO 4
<211> LENGTH: 20
<212> TYPE: DNA
<213> ORGANISM: Artificial sequence
<220> FEATURE:
<223> OTHER INFORMATION: GFP-SON-7/9

<400> SEQUENCE: 4
ctgttggatg gccaacactt                                              20

<210> SEQ ID NO 5
<211> LENGTH: 15
<212> TYPE: DNA
<213> ORGANISM: Artificial sequence
<220> FEATURE:
<223> OTHER INFORMATION: GFP-SON-8

<400> SEQUENCE: 5
gttccatggc caaca                                                   15

<210> SEQ ID NO 6
<211> LENGTH: 19
<212> TYPE: DNA
<213> ORGANISM: Artificial sequence
<220> FEATURE:
<223> OTHER INFORMATION: GFP target sequence

<400> SEQUENCE: 6
cctgttccat agccaacac                                               19

<210> SEQ ID NO 7
<211> LENGTH: 16
<212> TYPE: DNA
<213> ORGANISM: Artificial sequence
<220> FEATURE:
<223> OTHER INFORMATION: GFP target sequence

<400> SEQUENCE: 7
ttccatagcc aacact                                                  16

<210> SEQ ID NO 8
<211> LENGTH: 19
<212> TYPE: DNA
<213> ORGANISM: Artificial sequence
<220> FEATURE:
<223> OTHER INFORMATION: GFP target sequence

<400> SEQUENCE: 8
tacctgttcc atagccaac                                               19

<210> SEQ ID NO 9
<211> LENGTH: 20
<212> TYPE: DNA
<213> ORGANISM: Artificial sequence
<220> FEATURE:
<223> OTHER INFORMATION: GFP target sequence
```

<400> SEQUENCE: 9
tgttccatag ccaacacttg                                         20

<210> SEQ ID NO 10
<211> LENGTH: 22
<212> TYPE: DNA
<213> ORGANISM: Artificial sequence
<220> FEATURE:
<223> OTHER INFORMATION: GFP target sequence

<400> SEQUENCE: 10
cctgttccat agccaacact tg                                      22

<210> SEQ ID NO 11
<211> LENGTH: 28
<212> TYPE: DNA
<213> ORGANISM: Mus musculus

<400> SEQUENCE: 11
tttgccaaga agtagcgcct ttccctat                                28

<210> SEQ ID NO 12
<211> LENGTH: 13
<212> TYPE: DNA
<213> ORGANISM: Mus musculus

<400> SEQUENCE: 12
agaagtagcg cct                                                13

<210> SEQ ID NO 13
<211> LENGTH: 29
<212> TYPE: DNA
<213> ORGANISM: Mus musculus

<400> SEQUENCE: 13
ttttgccaag aagtagcgcc tttccctat                               29

<210> SEQ ID NO 14
<211> LENGTH: 45
<212> TYPE: DNA
<213> ORGANISM: Artificial sequence
<220> FEATURE:
<223> OTHER INFORMATION: ADAR94-1

<400> SEQUENCE: 14
gacugaggua cuccuuagag aaaggugcca cuucuuggca aagga             45

<210> SEQ ID NO 15
<211> LENGTH: 15
<212> TYPE: RNA
<213> ORGANISM: Artificial sequence
<220> FEATURE:
<223> OTHER INFORMATION: SON2

<400> SEQUENCE: 15
aagaaguggc accuu                                              15

<210> SEQ ID NO 16
<211> LENGTH: 19
<212> TYPE: DNA
<213> ORGANISM: Artificial sequence
<220> FEATURE:
<223> OTHER INFORMATION: forward primer Fw1_mSNRPA

<400> SEQUENCE: 16

```
gccttcgtgg agtttgaca                                                    19

<210> SEQ ID NO 17
<211> LENGTH: 20
<212> TYPE: DNA
<213> ORGANISM: Artificial sequence
<220> FEATURE:
<223> OTHER INFORMATION: reverse primer Rev1_mSNRPA

<400> SEQUENCE: 17
acacacggct ctgagaaggt                                                   20

<210> SEQ ID NO 18
<211> LENGTH: 21
<212> TYPE: DNA
<213> ORGANISM: Artificial sequence
<220> FEATURE:
<223> OTHER INFORMATION: sequence primer Snrp-1-Fw1

<400> SEQUENCE: 18
cgtggagttt gacaatgaag t                                                 21

<210> SEQ ID NO 19
<211> LENGTH: 20
<212> TYPE: DNA
<213> ORGANISM: Artificial sequence
<220> FEATURE:
<223> OTHER INFORMATION: forward primer Fw2_mSNRPA

<400> SEQUENCE: 19
gctctccatg ctcttcaacc                                                   20

<210> SEQ ID NO 20
<211> LENGTH: 18
<212> TYPE: DNA
<213> ORGANISM: Artificial sequence
<220> FEATURE:
<223> OTHER INFORMATION: reverse primer Rev2_mSNRPA

<400> SEQUENCE: 20
tcagggactg agccaagg                                                     18
```

OLIGONUCLEOTIDE COMPLEXES FOR USE IN RNA EDITING

RELATED APPLICATIONS

This application is a § 371 National Stage Application of PCT/EP2018/051202, filed Jan. 18, 2018, which claims priority to and the benefit of United Kingdom patent application No. 1700939.0, filed Jan. 19, 2017, and United Kingdom patent application No. 1707511.0, filed May 10, 2017, the entire disclosures of each of which are incorporated herein by reference for all purposes.

SEQUENCE LISTING

The instant application contains a Sequence Listing which has been submitted electronically in ASCII format and is hereby incorporated by reference in its entirety. Said ASCII copy, created on May 24, 2019, is named PQR-016_sequence_listing.txt and is 3,997 bytes in size.

FIELD OF THE INVENTION

The invention relates to the field of medicine. More in particular, it relates to the field of RNA editing, whereby an RNA sequence is targeted by an antisense oligonucleotide to correct a mutation, and wherein the antisense oligonucleotide is protected by a sense oligonucleotide to prevent degradation of the antisense oligonucleotide and thereby increase the efficiency and/or rate of RNA editing at the specified target site.

BACKGROUND OF THE INVENTION

RNA editing is a natural process through which eukaryotic cells alter the sequence of their RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms, such as *Caenorhabditis elegans*, to humans. Examples of RNA editing are adenosine (A) to inosine (I) and cytidine (C) to uridine (U) conversions through enzymes called adenosine deaminase and cytidine deaminase, respectively. The most extensively studied RNA editing system is the adenosine deaminase enzyme.

Adenosine deaminase is a multi-domain protein, comprising a recognition domain and a catalytic domain. The recognition domain recognizes a specific double-stranded RNA (dsRNA) sequence and/or conformation, whereas the catalytic domain converts an adenosine into an inosine in a nearby, more or less predefined, position in the target RNA, by deamination of the nucleobase. Inosine is read as guanosine by the translational machinery of the cell, meaning that, if an edited adenosine is in a coding region of an mRNA or pre-mRNA, it can recode the protein sequence. A-to-I conversions may also occur in 5' non-coding sequences of a target mRNA, creating new translational start sites upstream of the original start site, which gives rise to N-terminally extended proteins. Editing events also occur at 3' UTRs and affect miRNA-based regulation and polyadenylation. In addition, some A-to-I conversions take place in splice elements in introns or exons in pre-mRNAs, thereby altering the pattern of splicing. As a consequence, exons may be included or skipped. Adenosine deaminases are part of a family of enzymes referred to as Adenosine Deaminases acting on RNA (ADAR), including human deaminases hADAR1, hADAR2 and hADAR3.

The use of oligonucleotides to edit a target RNA applying an ADAR is known in the art (Montiel-Gonzalez et al. PNAS 2013, 110(45):18285-18290; Vogel et al. 2014. Angewandte Chemie Int Ed 53:267-271; Woolf et al. 1995. Proc Natl Acad Sci USA 92:8298-8302; WO 2016/097212). Montiel-Gonzalez et al. (2013) described the editing of a target RNA using a genetically engineered fusion protein, comprising an adenosine deaminase domain of the hADAR2 protein, fused to a bacteriophage lambda N protein, which recognises the boxB RNA hairpin sequence. The natural dsRNA binding domains of hADAR2 had been removed to eliminate the substrate recognition properties of the natural ADAR and replace it by the boxB recognition domain of lambda N-protein. The authors created an antisense oligonucleotide comprising a 'guide RNA' part that is complementary to the target sequence for editing, fused to a boxB portion for sequence specific recognition by the N-domain-deaminase fusion protein. By doing so, it was elegantly shown that the guide RNA oligonucleotide faithfully directed the adenosine deaminase fusion protein to the target site, resulting in guide RNA-directed site-specific A-to-I editing of the target RNA. The guide RNAs disclosed in Montiel-Gonzalez et al. (2013) are longer than 50 nucleotides in length. A disadvantage of such method in a therapeutic setting is the need for a fusion protein consisting of the boxB recognition domain of bacteriophage lambda N-protein, genetically fused to the adenosine deaminase domain of a truncated natural ADAR protein. It requires target cells to be either transduced with the fusion protein, which is a major hurdle, or that target cells are transfected with a nucleic acid construct encoding the engineered adenosine deaminase fusion protein for expression. The latter requirement constitutes no minor obstacle when editing is to be achieved in a multicellular organism, such as in therapy against human disease to correct a genetic disorder.

Vogel et al. (2014) disclosed editing of RNA coding for eCFP and Factor V Leiden, using a benzylguanine substituted guide RNA and a genetically engineered fusion protein, comprising the adenosine deaminase domains of ADAR1 or 2 (lacking the dsRNA binding domains) genetically fused to a SNAP-tag domain (an engineered 06-alkylguanine-DNA-alkyl transferase). Although the genetically engineered artificial deaminase fusion protein could be targeted to a desired editing site in the target RNAs in HeLa cells in culture, through its SNAP-tag domain which is covalently linked to a guide RNA through a 5'-terminal 06-benzylguanine modification, this system suffers from similar drawbacks as the genetically engineered ADARs described by Montiel-Gonzalez and colleagues, in that it is not clear how to apply the system without having to genetically modify the ADAR first and subsequently transfect the cells harboring the target RNA, to provide the cells with this genetically engineered protein. Clearly, this system is not readily adaptable for use in humans, e.g. in a therapeutic setting.

Woolf et al. (1995) disclosed a simpler approach, using relatively long single-stranded antisense RNA oligonucleotides (25-52 nucleotides in length) wherein the longer oligonucleotides (34-mer and 52-mer) could promote editing of the target RNA by endogenous ADAR because of the double-stranded nature of the target RNA and the hybridizing oligonucleotide. The oligonucleotides of Woolf et al. (1995) that were 100% complementary to the target RNA sequences only appeared to function in cell extracts or in amphibian (*Xenopus*) oocytes by microinjection, and suffered from severe lack of specificity: nearly all adenosines in the target RNA strand that was complementary to the antisense oligonucleotide were edited. An oligonucleotide wherein each nucleotide comprised a 2'O-methyl modification was tested and shown to be inactive. In order to provide stability against nucleases, another RNA oligonucleotide, modified with 2'-O-methyl-modified phosphorothioate nucleotides at the 5'- and 3'-terminal 5 nucleotides was also tested. It was shown that the central unmodified region of this oligonucleotide could promote editing of the target RNA by endogenous ADAR, with the terminal modifications providing protection against exonuclease degradation. Woolf et al. (1995) did not achieve deamination of a specific target adenosine in the target RNA sequence. Nearly all adenosines opposite an unmodified nucleotide in the antisense oligonucleotide were edited (therefore nearly all adenosines opposite nucleotides in the central unmodified region, if the 5'- and 3'-terminal 5 nucleotides of the antisense oligonucleotide were modified, or nearly all adenosines in the target RNA strand if no nucleotides were modified).

ADAR acts on any double stranded RNA (dsRNA). Through a process often referred to as 'promiscuous editing' the enzyme will edit multiple adenosines in a dsRNA. Hence, there is a need for methods and means that circumvent such promiscuous editing and that only target specified adenosines in a target RNA sequence. Vogel et al. (2014) showed that such off-target editing can be suppressed by using 2'-O-methyl-modified nucleotides in the oligonucleotide at positions opposite to the adenosines that should not be edited, and use a non-modified nucleotide directly opposite to the specifically targeted adenosine on the target RNA. However, the specific editing effect at the target nucleotide has not been shown to take place in that article without the use of recombinant ADAR enzymes that specifically form covalent bonds with the antisense oligonucleotide.

WO 2016/097212 discloses antisense oligonucleotides (AONs) for the targeted editing of RNA, wherein the AONs are characterized by a sequence that is complementary to a target RNA sequence (therein referred to as the 'targeting portion') and by the presence of a stem-loop structure (therein referred to as the 'recruitment portion'). Such oligonucleotides are referred to as 'axiomer AONs' or 'self-looping AONs'. The recruitment portion acts in recruiting a natural ADAR enzyme present in the cell to the dsRNA formed by hybridization of the target sequence with the targeting portion. Due to the recruitment portion there is no need for conjugated entities or presence of modified recombinant ADAR enzymes. WO 2016/097212 described the recruitment portion as being a stem-loop structure mimicking either a natural substrate (e.g. the GluR B receptor) or a Z-DNA structure known to be recognized by the dsRNA binding regions of ADAR enzymes. A stem-loop structure can be an intermolecular stem-loop structure, formed by two separate nucleic acid strands, or an intramolecular stem loop structure, formed within a single nucleic acid strand. The stem-loop structure of the recruitment portion as described in WO 2016/097212 is an intramolecular stem-loop structure, formed within the AON itself, and able to attract ADAR.

Patent application PCT/EP2017/065467 describes the use of antisense oligonucleotides for site-specific RNA editing, wherein the oligonucleotides comprise one or multiple mismatches (bulges) with the target nucleic acid and do not comprise a recruiting portion (as disclosed in WO 2016/097212) that is capable of binding ADAR.

Patent application PCT/EP2017/071912 describes similar AONs comprising a Central Triplet of 3 sequential nucleotides, wherein the nucleotide directly opposite the target adenosine is the middle nucleotide of the Central Triplet, wherein 1, 2 or 3 nucleotides in the Central Triplet comprise a sugar modification and/or a base modification to render the AON more stable and/or more effective in inducing deamination of the target adenosine; wherein the middle nucleotide does not have a 2'-O-alkyl modification.

Although it appears that numerous attempts have been made to use AONs in site-specific RNA editing, the AONs disclosed or described in the art suffer from a certain rate of instability in serum, which would make them ineffective in a therapeutic setting. For instance, the Central Triplet nucleotides opposite the target sites do not have a 2-O-alkyl modification, which in principle renders them unstable. Without wishing to be bound by theory, it is not unlikely that the instability is due to the absence of stability-inducing modifications in one or multiple nucleotides within the oligonucleotide. There appears to be a clear need in the art to solve the problem of instability of RNA editing AONs while maintaining (and thereby in fact increasing) the efficiency of site-directed RNA editing using (endogenous) ADAR proteins in the cell.

SUMMARY OF THE INVENTION

The invention relates to a double stranded oligonucleotide complex comprising an antisense oligonucleotide (AON) and a complementary sense oligonucleotide (SON) annealed to the AON via Watson-Crick base-pairing, for use in ADAR-mediated targeted deamination of a target adenosine in a target RNA sequence in a cell by an ADAR enzyme present in the cell. Preferably, the AON in said AON/SON complex comprises at least one nucleotide that is sensitive to nuclease dependent degradation, and the SON is complementary to the at least one nucleotide that is sensitive to nuclease dependent degradation. More preferably, the SON is complementary to all nucleotides in the AON that are sensitive to nuclease dependent degradation. In a further preferred aspect, the SON comprises a chemical modification assisting in improving a pharmacokinetic and/or a pharmacodynamics property of the complex, wherein the property is selected from the group consisting of: nuclease stability, cellular uptake, intracellular trafficking, and ADAR-mediated AON-guided editing of a target RNA in a cell comprising ADAR.

The invention also relates to a pharmaceutical composition comprising the double stranded oligonucleotide complex according to the invention, and a pharmaceutically acceptable carrier. In yet another aspect, the invention relates to a double stranded oligonucleotide complex according to the invention, or the pharmaceutical composition according to the invention, for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

The invention further relates to a method for the deamination of at least one specific target adenosine present in a target RNA sequence in a cell, the method comprising the steps of: providing the cell with a double stranded oligonucleotide complex according to the invention; allowing uptake by the cell of the AON; allowing annealing of the AON to the target RNA sequence; allowing a mammalian ADAR enzyme comprising a natural dsRNA binding domain as found in the wild type enzyme to deaminate the target adenosine in the target RNA sequence to an inosine; and optionally identifying the presence of the inosine in the RNA sequence. The optional step in the method of the present invention preferably comprises: sequencing the target RNA sequence; assessing the presence of a functional, elongated, full length and/or wild type protein when the target adenosine is located in a UGA or UAG stop codon, which is edited to a UGG codon through the deamination; assessing the presence of a functional, elongated, full length and/or wild type protein when two target adenosines are located in a UAA stop codon, which is edited to a UGG codon through the deamination of both target adenosines; assessing whether splicing of the pre-mRNA was altered by the deamination; or using a functional read-out, wherein the target RNA after the deamination encodes a functional, full length, elongated and/or wild type protein.

In another aspect the invention relates to a double stranded oligonucleotide complex or the method according to the invention, wherein the target RNA sequence encodes CFTR (e.g. to edit a 1784G>A mutation), CEP290 (e.g. to edit a c.2991+1655A>G mutation), alpha1-antitrypsin (A1AT; e.g. to edit a 9989G>A mutation; or a 1096G>A mutation), Guanine Nucleotide Binding Protein (GNAQ; e.g. to edit a 548G>A mutation), or LRRK2 (e.g. to edit a G6055 mutation), or wherein the target RNA is encoded by the IDUA gene (e.g. to edit a c.1205G>A (W402X) mutation).

The invention also relates to a method for the deamination of a specific target adenosine present in a target RNA sequence in a cell, said method comprising the steps of: providing said cell with an AON/SON complex according to the invention; allowing annealing of said AON to the target RNA sequence; allowing a mammalian ADAR enzyme comprising a natural dsRNA binding domain as found in the wild type enzyme to deaminate said target adenosine in said target RNA sequence to an inosine; and identifying the presence of said inosine in the RNA sequence.

BRIEF DESCRIPTION OF THE DRAWINGS

FIG. 1 shows (A) the 3' to 5' sequence of the ADAR59-2 antisense oligonucleotide (AON) with the Central Triplet underlined, and the nine sense oligonucleotides (SONs, all 5' to 3'), with their respective SEQ ID NO's, that were initially tested for protecting the AON from degradation; (B) the specific modifications and content of the different oligonucleotides is shown; PMO=phosphorodiamidate; the asterisk indicates a phosphorothiate linkage.

FIG. 2 shows the results of the stability assays. Upper two panels: SONs were analysed in 15% denaturing Urea-PAGE gels. CTL-samples were incubated in 1×PBS and RX-samples in cell culture medium supplemented with 15% FBS for 30 min at 37° C. Lower two panels: ADAR59-2 and AON-SON complexes were analysed in 12% denaturing Urea-PAGE gels.

FIG. 4 shows representative sequencing results from SNU-475 cells transfected with low amounts of GFPstop57 construct and wherein the cells were subsequently transfected with ADAR59-2 alone (middle panel) or in combination with SON-6 (right panel). NT=non-transfected with ADAR59-2 or SON-6 (left panel). The arrow indicates the targeted adenosine. The sequence represented by the peaks in each of the three figures is 5'-CCTGTTCCAT AGCCAACACTTG-3' (SEQ ID NO: 10), with the target adenosine underlined.

DETAILED DESCRIPTION OF THE INVENTION

Figure 3:
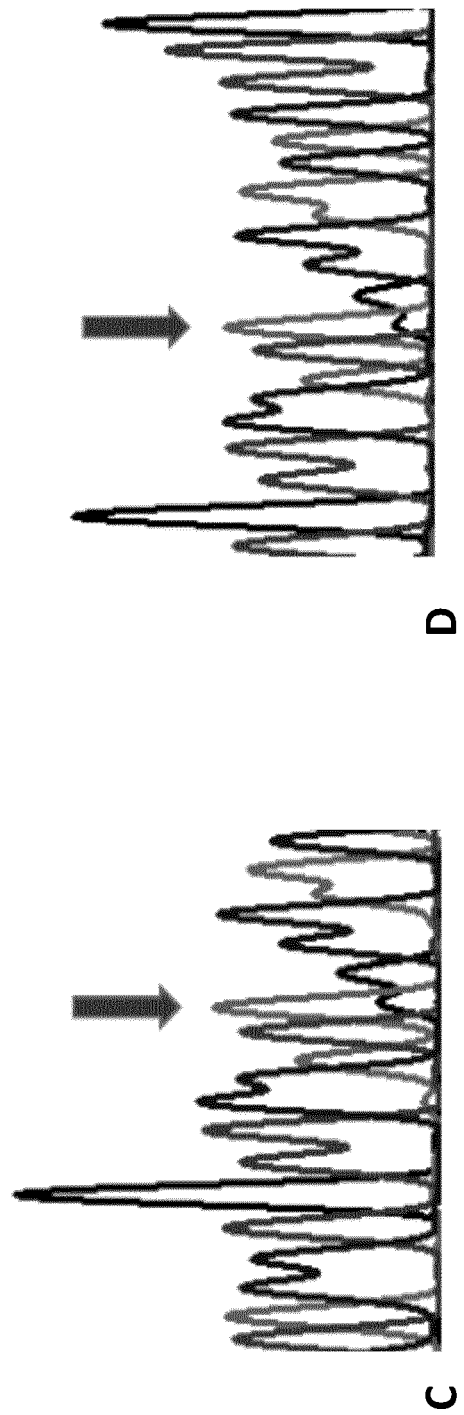
FIG. 3 shows representative sequencing results from MCF-7 cells expressing a GFPstop57 construct (as explained in more detail in the examples), transfected with ADAR59-2 AON alone or with the indicated AON/SON complexes. The arrow indicates the targeted adenosine. The sequence represented by the peaks is 5'-CCTGTTCCAT AGCCAACAC-3' (SEQ ID NO: 6) in A, 5'-TTCCAT AGCCAACACT-3' (SEQ ID NO: 7) in B, 5'-TACCTGTTC-CATAGCCAAC-3' (SEQ ID NO: 8) in C, and 5'-TGTTC-CATAGCCAACACTTG-3' (SEQ ID NO: 9) in D, with the target adenosine underlined.

The present invention relates to protecting sense oligonucleotides (SONs) for use in RNA editing. More specifically, it relates to the use of SONs in protecting antisense oligonucleotides (AONs) that are used for ADAR-mediated editing (herein also referred to as "ADAR-editing AONs", "ADAR-recruiting AONs" or briefly "editing AONs", or even more briefly "AONs") from degradation, such that the site-specific RNA editing efficiency or rate through AONs is increased. Additional advantages of annealing editing AONs with complementary SONs will become apparent from the detailed description of the invention.

Previously, it has been described how adenosine deaminases acting on RNA (ADARs) can be specifically harnessed to induce adenosine-to-inosine (A-to-I) editing at desired nucleotides using AONs. The present invention discloses methods and means for increasing the stability and thereby increasing RNA editing activity of such AONs by annealing them to protecting SONs (hereinafter also referred to as "SONs", for brevity) before they enter the cell. It is demonstrated that an ADAR-recruiting AON can be readily annealed to a protecting SON containing a variety of chemical modifications, and that the resulting complexes induce more efficient RNA editing than the "naked" unprotected AON.

Various chemical modifications can be used to increase the stability and cellular uptake of AONs (GB 1614858.7, GB 1616374.3 and GB 1621467.8; reviews in Sharma V K and Watts J K. 2015. Future Med Chem 7:2221-2242; Juliano R L. 2016. Nucleic Acids Res 44:6518-6548). These modifications are introduced either in the phosphate backbone or the sugar moiety of the oligonucleotide. A phosphorothioate backbone modification increases not only stability but also stimulates protein binding, which leads to reduced renal clearing in vivo. A 2'-O-methyl modification in the sugar decreases sensitivity to nucleases, and has been shown to reduce off-targeting and immune responses. The sugar-phosphate backbone can also be made completely devoid of negative charge by replacing it with phosphorodiamidate morpholino (PMO) chemistry.

It is known in the art that the inherent instability of single-stranded oligonucleotides can be masked by complexing them with a variety of compounds. One approach is to formulate the AON into a nanoparticle (e.g. lipids or polymers) prior to exposing the nucleic acid to conditions that may induce degradation. However, the use of such compounds adds in the costs and complexity of formulating pharmaceutical active ingredients. The present invention solves this by annealing the active and ADAR editing AON with a complementary SON through Watson-Crick base-pairing, forming a duplex. This was unexpected because it was envisioned that the AON/SON complex may in fact be too stable and because of its double strand nature interfere with the RNA editing induction that was seen with the AON alone. This appeared not the case. In fact, the RNA editing efficiency (rate) was increased and is believed to be a result of the fact that the AON/SON complex during the presence in the culture medium, during uptake in the cell and/or trafficking through the cell towards the AON target is less prone to degradation attacks from RNA and DNA nucleases. It is also envisioned that the nature of the SONs, such as their chemical composition and/or charge, has a beneficial effect on cellular uptake and/or intracellular trafficking of the AON/SON complex to the productive cellular compartment. This may be due to its overall chemical characteristics and/or by mediation of proteins bound to them (such as receptors at the cell surface or proteins that facilitate intracellular sorting).

Analysis of natural targets of ADAR enzymes has indicated that these generally include mismatches between the two strands that form the RNA helix edited by ADAR1 or 2. It has been suggested that these mismatches enhance the specificity of the editing reaction (Stefl et al. 2006. Structure 14(2):345-355; Tian et al. 2011. Nucleic Acids Res 39(13): 5669-5681). Characterization of optimal patterns of paired/ mismatched nucleotides between the AONs and the target RNA also appears crucial for development of efficient ADAR-based AON therapy. The use of specific nucleotide modifications at predefined spots ensures—to a certain level—stability as well as proper ADAR binding and activity. These changes may vary and may include modifications in the backbone of the AON, in the sugar moiety of the nucleotides as well as in the nucleobases. They may also be variably distributed throughout the sequence of the AON. Specific modifications may be needed to support interactions of different amino acid residues within the RNA-binding domains of ADAR enzymes, as well as those in the deaminase domain. For example, phosphorothioate linkages between nucleotides or 2'-O-methyl modifications may be tolerated in some parts of the AON, while in other parts they should be avoided so as not to disrupt crucial interactions of the ADAR enzyme with the phosphate and 2'—OH groups. Part of these design rules are guided by the published structures of ADAR2, while others have to be defined empirically. Different preferences may exist for ADAR1 and ADAR2. The modifications should also be selected such that they prevent degradation of the AONs. Specific nucleotide modifications may also be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014. Nucleic Acids Res 42(10):e87). The recent structural analysis of ADAR2 deaminase domain hints at the possibility of enhancing editing by careful selection of the nucleotides that are opposite to the target trinucleotide. For example, the 5'-CAA-3' target sequence, paired to a 3'-GCU-5' sequence on the opposing strand (with the A-C mismatch formed in the middle), is disfavored because the guanosine base sterically clashes with an amino acid side chain of ADAR2. Inosine could potentially fit better into this position without causing steric clashes, while still retaining the base-pairing potential to the opposing cytosine. Modifications that could enhance activity of suboptimal sequences include the use of backbone modifications that increase the flexibility of the AON or, conversely, force it into a conformation that favors editing. However, depending on the sequence context of the target, it may not be possible to design editing AONs containing nucleotide modifications that allow both optimal editing efficiency and optimal stability. The protective SONs may be used to enhance the stability aspect, thus removing these design constraints from the AON itself, allowing the AON to be designed with modifications for optimal ADAR editing function.

The protective SONs according to the invention can in principle be used with any editing AON, such as those described in WO 2016/097212, PCT/EP2017/065467, and PCT/EP2017/071912 (the relevant parts whereof are incorporated herein) or any other editing AON that could benefit from the protective or other beneficial characteristics of the complementary SON. For example, if editing AONs are being used with a recruiting portion and a targeting portion (as described in the published PCT-application mentioned above), the SON should preferably be complementary to (part of) the targeting portion. For editing AONs without the internal stem-loop structure designed for ADAR-recruitment, such as those described in the three unpublished GB-applications, a SON may anneal to any portion of the AON that is vulnerable to degradation, such as those portions having 2'-OH ribose as backbone.

Various chemistries and modifications are known in the field of oligonucleotides that can be readily used for both the AON and the SON. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. The internucleotidic linkages may be replaced in full or in part by peptidic linkages to yield in peptidonucleic acid sequences and the like. Alternatively, or in addition, the nucleobases may be modified by (de)amination, to yield inosine or 2'6'-diaminopurines and the like. A further modification may be methylation of the C5 in the cytidine moiety of the nucleotide, to reduce potential immunogenic properties known to be associated with CpG sequences. In a preferred aspect the oligonucleotides of the present invention have one, two, three, four or more phosphorothioate linkages between the most terminal nucleotides of the oligonucleotide (hence, preferably at both the 5' and 3' end), which means that in the case of four phosphorothioate linkages, the ultimate 5 nucleotides are linked accordingly. It will be understood by the skilled person that the number of such linkages may vary on each end, depending on the target sequence, or based on other aspects, such as toxicity, but predominantly on whether RNA editing can still be achieved when present in a double stranded AON/SON complex as disclosed herein. The ribose sugar may be modified by substitution of the 2'-0 atom with alkyl (e.g. 2'-O-methyl), alkynyl (2'-O-alkynyl), alkenyl (2'-O-alkenyl), alkoxyalkyl (e.g. methoxyethyl, 2'-MOE) groups, or other substituent. Preferred substituents of the 2' OH group are a methyl, methoxyethyl or 3,3'-dimethylallyl group. The latter is known for its property to inhibit nuclease sensitivity due to its bulkiness, while improving efficiency of hybridization (Angus and Sproat 1993. FEBS 325:123-7). Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art.

The terms 'adenine', 'guanine', 'cytosine', 'thymine', 'uracil' and 'hypoxanthine' (the nucleobase in inosine) as used herein refer to the nucleobases as such. The terms 'adenosine', 'guanosine', 'cytidine', 'thymidine', 'uridine' and 'inosine', refer to the nucleobases linked to the (deoxy) ribosyl sugar. The term 'nucleoside' refers to the nucleobase linked to the (deoxy)ribosyl sugar. The term 'nucleotide' refers to the respective nucleobase-(deoxy)ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like. Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide. Sometimes the terms nucleobase, nucleoside and nucleotide are used interchangeably, unless the context clearly requires differently. Whenever reference is made to an 'oligonucleotide', both oligoribonucleotides and deoxyoligoribonucleotides are meant unless the context dictates otherwise. Whenever reference is made to an 'oligoribonucleotide' it may comprise the bases A, G, C, U or I. Whenever reference is made to a 'deoxyoligoribonucleotide' it may comprise the bases A, G, C, T or I. In a preferred aspect, an AON in the AON/SON complex of the present invention is an oligoribonucleotide that may comprise chemical modifications. Whenever reference is made to nucleotides in the oligonucleotide construct, such as cytosine, then 5-methylcytosine, 5-hydroxymethylcytosine, Pyrrolocytidine, and β-D-Glucosyl-5-hydroxy-methylcytosine are included. When reference is made to adenine, then 2-aminopurine, 2,6-diaminopurine, 3-deazaadenosine, 7-deazaadenosine, 8-azidoadenosine, 8-methyladenosine, 7-aminomethyl-7-deazaguanosine, 7-deazaguanosine, N6-Methyladenine and 7-methyladenine are included. When reference is made to uracil, then 5-methoxyuracil, 5-methyluracil, dihydrouracil, pseudouracil, and thienouracil, dihydrouracil, 4-thiouracil and 5-hydroxymethyluracil are included. When reference is made to guanine, then 7-methylguanosine, 8-aza-7-deazaguanosine, thienoguanosine and 1-methylguanine are included. Whenever reference is made to nucleosides or nucleotides, then ribofuranose derivatives, such as 2'-deoxy, 2'-hydroxy, 2-fluororibose and 2'-O-substituted variants, such as 2'-O-methyl, are included, as well as other modifications, including 2'-4' bridged variants. Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term 'comprising' encompasses 'including' as well as 'consisting', e.g. a composition 'comprising X' may consist exclusively of X or may include something additional, e.g. X+Y. The term 'about' in relation to a numerical value x is optional and means, e.g. x±10%. The word 'substantially' does not exclude 'completely', e.g. a composition which is 'substantially free from Y' may be completely free from Y. Where relevant, the word 'substantially' may be omitted from the definition of the invention. The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand. References to 'hybridisation' typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity.

The term 'mismatch' is used herein to refer to opposing nucleotides in a double stranded RNA complex which do not form perfect base pairs according to the Watson-Crick base pairing rules. Mismatch base pairs are G-A, C-A, U-C, A-A, G-G, C-C, U-U base pairs. In certain instances, AONs that are used for RNA editing comprise 0, 1, 2 or 3 mismatches with their target sequence, wherein a single mismatch may comprise several sequential nucleotides. Wobble base pairs are: G-U, I-U, I-A, and I-C base pairs.

An oligonucleotide may be chemically modified partly or almost in its entirety, for example by providing some or all nucleotides with a 2'-O-methylated sugar moiety (2'-OMe). However, in the AON, the nucleotide opposite the target adenosine generally does not comprise the 2'-OMe modification, and in yet another aspect, at least one and in another aspect both the two neighbouring nucleotides flanking each nucleotide opposing the target adenosine further do not comprise the 2'-OMe modification. These three nucleotides are also together referred to as the 'Central Triplet' (as outlined herein), wherein none of the three nucleotides in the Central Triplet is 2'-OMe modified. Complete modification, wherein all nucleotides within the AON hold a 2'-OMe modification results in a non-functional oligonucleotide as far as RNA editing goes, presumably because it hinders the ADAR activity at the targeted position. In general, an adenosine in a target RNA can be protected from editing by providing an opposing nucleotide with a 2'-OMe group, or by providing a guanine or adenine as opposing base, as these two nucleobases are also able to reduce editing of the opposing adenosine. The fact that 1, 2 or 3 nucleotides in the Central Triplet do often not contain a 2'-OMe modification renders the AON more vulnerable for breakdown. The inventors of the present invention have sought means to prevent such breakdown and succeeded by using a complementary SON that anneals (binds) to the AON and thereby prevents breakdown, without impairing overall RNA editing efficiency. Hence, the AON, which is one partner in the AON/SON complex is the 'guidemer' to ensure RNA editing by an ADAR enzyme present in the cell. The role of the SON, which is the other partner in the AON/SON complex according to the present invention, is to stabilize the AON and to lower the risk of breakdown of the AON by enzymes in the cell culture medium, in the surrounding medium or tissue of the cell or inside the cell. It should be noted that some oligonucleotides that partner in a double stranded complex are more firmly attached to each other than others, depending for instance on the GC content, the (synthetic) chemical modifications that are introduced, length, etc. The binding of the SON to the AON should not be so strong that RNA editing caused by the AON on the target RNA is diminished (possibly because of the strong binding between SON and AON). Some inhibition of direct AON function can be expected due to a subpopulation of SONs not being released from the AONs, but this is likely more than compensated by the increased stability and/or uptake of the complex, and hence an overall increase in the concentration of available AON in the relevant cellular compartment. The inventors of the present invention have found certain SONs (that do attach to the AONs) that do actually not hamper RNA editing and in fact provide an increase in final RNA editing rate because the interaction with the targeting AON results in less breakdown of the AON. The final functional readout is, and should be, the improved (increased, more efficient) RNA editing of the target RNA molecule, which is presumably caused by lowered breakdown of the AON that is used for that purpose, as outlined by the present invention, although a positive effect on other aspects of the pharmacokinetics or pharmacodynamics of the AON/SON complex, such as cellular uptake and/or intracellular trafficking should not be ruled out. Hence, according to the invention, a double stranded complex comprising an AON and a SON as disclosed herein, should give an increase in the level of RNA editing in comparison to the situation wherein the AON is used without being complexed to a (synthetic) opposing SON.

The invention relates to a double stranded oligonucleotide complex comprising an antisense oligonucleotide (AON) and a complementary sense oligonucleotide (SON) annealed to the AON via Watson-Crick base-pairing, for use in ADAR-mediated targeted deamination of a target adenosine in a target RNA sequence in a cell by an ADAR enzyme present in the cell. In a preferred embodiment, the AON comprises at least one nucleotide that is sensitive to nuclease dependent degradation, and in a further preferred embodiment the SON is complementary to the at least one nucleotide that is sensitive to nuclease dependent degradation. In yet a further preferred embodiment, the SON is complementary to all nucleotides in the AON that are sensitive to nuclease dependent degradation. Nucleotides that are sensitive for nuclease dependent breakdown (that may be present in the AON) and that may hamper the efficiency of RNA editing, are well-known in the art. Examples are phosphodiester internucleosidic linkages, 2'-OH riboses, etc. When such nuclease-sensitive moieties are present in the AON that is applied for RNA editing, the AON will benefit from the SON as described herein and AON comprising such moieties are therefore part of the invention. In a preferred embodiment, the SON comprises a chemical modification assisting in improving a pharmacokinetic and/or a pharmacodynamics property of the complex, wherein the property is selected from the group consisting of: nuclease stability, cellular uptake, intracellular trafficking, and ADAR-mediated AON-guided editing of a target RNA in a cell comprising ADAR. In another preferred embodiment, the SON within said AON/SON complex according to the invention comprises a backbone with one or more phosphorothioate internucleosidic linkages and/or one or more 2'-OMe modified riboses. The SON may be of any length and may be longer, shorter or of equal length as the Aon that needs to be protected. However, in a particular preferred embodiment, the SON is equally long as, or shorter than the AON. The SON may be as short as 4 nucleotides, for instance when the only nuclease sensitive moieties in the AON are within the Central Triplet as discussed herein and the SON is at least complementary to the nucleotides in the Central Triplet that are nuclease breakdown sensitive. Hence, a SON in an AON/SON complex according to the present invention may comprise 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. In one particular preferred embodiment, the SON is fully complementary to the AON, which may mean that the AON and SON are of equal length and all nucleotides pair, but it may also mean that all nucleotides of the SON pair with their respective nucleotides in the AON, but that the AON is longer than the SON. In yet another aspect, the SON in the AON/SON complex of the present invention comprises one or more mismatches or wobbles when annealed to the AON. In a preferred embodiment, the SON comprises one or more nucleotides which are RNA, DNA, LNA or BNA or combinations thereof, optionally chemically modified in the backbone. In one particular aspect, the SON, when getting shorter than 10 nucleotides, is preferably a full LNA oligonucleotide, for instance when the SON consists of 4, 5, 6, 7, 8, 9 or 10 nucleotides. In a further preferred embodiment, the AON comprises at least one sugar modification selected from the group consisting of deoxyribose (DNA), Unlocked Nucleic Acid (UNA) and 2'-fluororibose. In yet another preferred aspect, the SON comprises only RNA nucleotides, optionally chemically modified in the backbone.

The invention furthermore relates to a pharmaceutical composition comprising the double stranded oligonucleotide complex according to the invention, and a pharmaceutically acceptable carrier. The invention also relates to a double stranded oligonucleotide complex according to the invention, or a pharmaceutical composition according to the invention, for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

In yet another aspect, the invention relates to the use of the double stranded oligonucleotide complex according to the invention in the manufacture of a medicament for the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

In another embodiment, the invention relates to a method for the deamination of at least one specific target adenosine present in a target RNA sequence in a cell, the method comprising the steps of: providing the cell with a double stranded oligonucleotide complex according to the invention; allowing uptake by the cell of the AON; allowing annealing of the AON to the target RNA sequence; allowing a mammalian ADAR enzyme comprising a natural dsRNA binding domain as found in the wild type enzyme to deaminate the target adenosine in the target RNA sequence to an inosine; and optionally identifying the presence of the inosine in the RNA sequence. Preferably, optional final step of the method according to the invention comprises: sequencing the target RNA sequence; assessing the presence of a functional, elongated, full length and/or wild type protein when the target adenosine is located in a UGA or UAG stop codon, which is edited to a UGG codon through the deamination; assessing the presence of a functional, elongated, full length and/or wild type protein when two target adenosines are located in a UAA stop codon, which is edited to a UGG codon through the deamination of both target adenosines; assessing whether splicing of the pre-mRNA was altered by the deamination; or using a functional read-out, wherein the target RNA after the deamination encodes a functional, full length, elongated and/or wild type protein. In yet another embodiment, the invention relates to a double stranded oligonucleotide complex or method according to the invention, wherein the target RNA sequence encodes CFTR (e.g. to edit a 1784G>A mutation), CEP290 (e.g. to edit a c.2991+1655A>G mutation), alpha1-antitrypsin (A1AT; e.g. to edit a 9989G>A mutation; or a 1096G>A mutation), Guanine Nucleotide Binding Protein (GNAQ; e.g. to edit a 548G>A mutation), or LRRK2 (e.g. to edit a G6055 mutation), or wherein the target RNA is encoded by the IDUA gene (e.g. to edit a c.1205G>A (W402X) mutation).

SONs in the AON/SON complexes according to the invention should to a certain extent be complementary to the corresponding editing AON. SONs may be 100% complementary to an AON (all nucleotides in the SON have an opposite Watson-Crick complementary nucleotide in the AON). In another aspect, all nucleotides in the AON have an opposite Watson-Crick complementary nucleotide in the SON. The SON may be of the same size as the AON (with or without maximum complementarity). SONs may be shorter or longer than the corresponding AON, and complementarity may be reduced to lower levels (and thereby generating a reduction of melting temperature, Tm) by introduction of mismatches or wobbles between the SON and the AON, depending on the need and degree of editing that is needed and achieved. Minimum and maximum complementarity may be determined empirically, using a serum stability and/or editing assay as described herein and with methods known to the person skilled in the art. The ideal level of complementarity may depend on the disease or the target tissue and/or formulation and administration details. Since the AON/SON complexes according to the invention are intended for therapeutic use in humans, complementarity ideally ensures that the AON and corresponding SON are at least in an annealed state under physiological conditions, meaning body temperature and physiological salt concentration. As will be readily understood by a person skilled in the art, the route of administration may also play a role, as different body parts or tissues may vary somewhat in their local temperature and salt concentration. The chemical make-up of the SON may also define the minimal or the maximal complementarity of the SON. While it is known by those of skill in the art that the strength of Watson-Crick base-pairing depends, among other things, on GC content, the percentage of complementarity, the annealing SON strands being RNA, DNA, LNA or BNA, it will be readily apparent that these factors determine minimal or maximal complementarity and that absolute numbers for minimum or maximum complementarity are hard to give. It should be understood that longer stretches of complementarity may not always be better than shorter, as stronger Watson-Crick base pairing may hamper the SON from coming off, thereby slowing down target RNA finding and/or Watson-Crick base pairing of the AON with the complementary target RNA, which are all requirements for AON guided editing to take place. Hence, the optimal level of complementarity will require some empirical testing for each RNA target.

Preferred SONs increase editing of the target RNA, as the ultimate goal is to improve AON-targeted and ADAR-mediated editing of the target RNA. "Improved" or "increased" always means in comparison to the unprotected (or 'naked') AON, all other parameters and assay conditions remaining equal. While increased editing is believed to be due to increased stability, factors such as improved cellular uptake, endosomal release, productive intracellular compartment trafficking or interactions of the AON/SON complex with the target RNA or ADAR or other factors may also contribute to the pharmacokinetics or pharmacodynamics and, ultimately on editing efficiency. One example is the addition of PS-groups in the backbone of the SON, which is believed to lead to binding of the complex to albumin, ultimately leading to higher retention times in the plasma. This in turn may lead to better cellular uptake and higher concentrations of the editing AON in the productive compartments for editing.

It should therefore be understood, that any improvement in editing by the editing AON brought about by the SONs according to the invention is covered by the present invention, regardless of how such improvement is brought about.

The AON used for RNA editing should normally be longer than 10, 11, 12, 13, 14, 15, 16, 17, or 18 nucleotides, and preferably shorter than 100, 60, or 50 nucleotides. Preferably, and RNA editing AON comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. The size of the protecting SON may vary and the SON may be shorter than the opposing AON. Preferably, the SON comprises one or more nucleotides opposite the nucleotides in the AON that are not fully protected against degradation. For example, when the three nucleotides in the Central Triplet in the AON are unprotected, for instance by the lack of 2'-O-methyl groups, the protection providing SON in the AON/SON complex covers at least the three nucleotides in the Central Triplet; or in other words, contains nucleotides that are opposite the three nucleotides in the Central Triplet in the AON/SON complex. It should be clear that any nucleotide in the AON (also those that are not part of the Central Triplet), that is prone to degradation may benefit if covered by the annealing SON. The length of the SON is preferably at least 10 nucleotides, more preferably in the range of 15-20 nucleotides (e.g. 15, 16, 17, 18, 19 or 20 nucleotides), especially when the Central Triplet in the AON are the only three nucleotides in the AON that do not contain a 2-O-alkyl modification. The skilled person would readily understand that when additional nucleotides in the AON are prone to breakdown, the SON may be longer to also cover those additional nucleotides in the AON, as long as the RNA editing efficiency of the AON is not hampered by the SON or the length and/or modifications of the SON.

It is known in the art that RNA editing entities (such as human ADAR enzymes) edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 and 2 can be increased by ensuring a number of mismatches in the dsRNA, which presumably help to position the dsRNA binding domains in a way that has not been clearly defined yet. Additionally, the deamination reaction itself can be enhanced by providing an AON that comprises a mismatch opposite the adenosine to be edited. The mismatch is preferably created by providing a targeting portion having a cytidine opposite the adenosine to be edited. As an alternative, also uridines may be used opposite the adenosine, which, understandably, will not result in a 'mismatch' because U and A pair. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct. After the mismatch has been resolved due to editing, the substrate is released and the oligonucleotide construct-editing entity complex is released from the target RNA sequence, which then becomes available for downstream biochemical processes, such as splicing and translation.

An RNA editing AON that is an oligoribonucleotide, or a SON that is RNA, will usually comprise the normal nucleotides A, G, U and C, but may also include inosine (I), for example instead of one or more G nucleotides. To prevent undesired editing of adenosines in the target RNA sequence in the region of overlap with the oligonucleotide construct, the oligonucleotide may be chemically modified. 2'-O-methylation of the ribosyl-moiety of a nucleoside opposite an adenosine in the target RNA sequence dramatically reduces deamination of that adenosine by ADAR (Vogel et al. 2014). Hence, by including 2'-methoxy (2'-OMe) nucleotides in desired portions of the oligonucleotide construct, the specificity of editing is dramatically improved. Other 2'-O substitutions of the ribosyl moiety, such as 2'-methoxyethyl (2'-MOE) and 2'-O-dimethylallyl groups may also reduce unwanted editing of the corresponding (opposite) adenosine in the target RNA sequence. Other chemical modifications (as discussed above) are readily available to the person having ordinary skill in the art of oligonucleotide synthesis and design.

The invention concerns the modification of target RNA sequences in eukaryotic, preferably metazoan, more preferably mammalian cells. In principle the invention can be used with cells from any mammalian species, but it is preferably used with a human cell. The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject. Such cells include but are not limited to epithelial cells of the lung or the gastrointestinal tract, cells of the reproductive organs, muscle cells, cells of the eye, cells of the skin, cells from tissues and organs such as liver, kidney, pancreas, immune cells, cancerous cells, gland cells, brain cells, and the like. The invention can also be used with mammalian cells which are not naturally present in an organism e.g. with a cell line or with an embryonic stem (ES) cell. The invention can be used with various types of stem cell, including pluripotent stem cells, totipotent stem cells, embryonic stem cells, induced pluripotent stem cells, etc. The cell can be located in vitro or in vivo. One advantage of the invention is that it can be used with cells in situ in a living organism, but it can also be used with cells in culture. In some embodiments cells are treated ex vivo and are then introduced into a living organism (e.g. re-introduced into an organism from whom they were originally derived). The invention can also be used to edit target RNA sequences in cells within a so-called organoid. Organoids can be thought of as three-dimensional in vitro-derived tissues but are driven using specific conditions to generate individual, isolated tissues. In a therapeutic setting they are useful because they can be derived in vitro from a patient's cells, and the organoids can then be re-introduced to the patient as autologous material which is less likely to be rejected than a normal transplant.

The cell to be treated will generally have a genetic mutation. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations. Genes containing mutations of particular interest are discussed below. A mutation to be reverted through RNA editing may have arisen on the level of the chromosome or some other form of DNA, such as mitochondrial DNA, or RNA, including pre-mRNA, ribosomal RNA or mitochondrial RNA. A change to be made may be in a target RNA of a pathogen, including fungi, yeasts, parasites, kinetoplastids, bacteria, phages, viruses etc. with which the cell or subject has been infected. Subsequently, the editing may take place on the RNA level on a target sequence inside such cell, subject or pathogen. Certain pathogens, such as viruses, release their nucleic acid, DNA or RNA into the cell of the infected host (cell). Other pathogens reside or circulate in the infected host. The oligonucleotide constructs of the invention may be used to edit target RNA sequences residing in a cell of the infected eukaryotic host, or to edit a RNA sequence inside the cell of a pathogen residing or circulating in the eukaryotic host, as long as the cells where the editing is to take place contain an editing entity compatible with the oligonucleotide construct administered thereto.

Without wishing to be bound by theory, the RNA editing through hADAR1 and hADAR2 is thought to take place on primary transcripts in the nucleus, during transcription or splicing, or in the cytoplasm, where e.g. mature mRNA, miRNA or other ncRNA can be edited. Different isoforms of the editing enzymes are known to localize differentially, e.g. with hADAR1 p110 found mostly in the nucleus, and hADAR1 p150 in the cytoplasm. The RNA editing by cytidine deaminases is thought to take place on the mRNA level. Editing of mitochondrial RNA codons or non-coding sequences in mature mRNAs is not excluded.

The invention allows now to make a change in a target RNA sequence in a eukaryotic cell through the use of an AON that is capable of targeting a site to be edited and recruiting RNA editing entities resident in the cell to bring about the editing reaction(s), wherein the AON is complexed to a sense (complementary) oligonucleotide. 'Complexed' is herein defined as that the AON is annealed (bound) to the SON before it enters the cell. It is not known when or where the SON is detached from the AON such that the AON can cause the RNA editing to happen. The detachment may take place upon cell entry or during trafficking through the cell, or briefly before the AON reaches the target sequence, or following an initial binding of the AON to the target RNA through parts of the AON that are not bound by the SON.

Preferred editing reactions brought about by the AONs that are complexed to the SON for efficient editing, are adenosine deaminations and cytidine deaminations, converting adenosines into inosines and cytidines into uridines, respectively. The changes may be in 5' or 3' untranslated regions of a target RNA, in (cryptic) splice sites, in exons (changing amino acids in protein translated from the target RNA, codon usage or splicing behaviour by changing exonic splicing silencers or enhancers, by introducing or removing start or stop codons), in introns (changing splicing by altering intronic splicing silencers or intronic splicing enhancers, branch points) and in general in any region affecting RNA stability, structure or functioning. The target RNA sequence may comprise a mutation that one may wish to correct or alter, such as a point mutation (a transition or a transversion). Alternatively, the target RNA sequence is deliberately mutated to create an altered phenotype (or genotype, in case of RNA based organisms, such as RNA viruses), where there was no mutation before. For example cell lines or animals may be made which carry changes (mutations) in a target RNA sequence, which may be used in assays or as (animal, organoid, etcetera) model systems to study disease, test experimental compounds against disease, and the like. The oligonucleotide constructs and methods according to the invention may be used in high throughput screening systems (in arrayed format) for making cell banks with a large variety of target RNAs, for example coding for a large variety of protein isoforms, for further experimentation, including compound screening, protein engineering and the like. The target RNA may be any cellular or viral RNA sequence, but is more usually a pre-mRNA or an mRNA with a protein coding function.

Purely for ease of reference, and without the intention to limit the invention, Table 1 is provided to illustrate the potential codon changes that can be brought about by adenosine deaminase editing directed by oligonucleotides of the invention. Table 1 particularly should not be interpreted as a limitation of the applicability of the invention to coding sequences in any RNA; as pointed out already, the invention can be practised on any RNA target comprising an adenosine, whether in a coding region, an intron, a non-coding exon (such as a 5'- or 3' untranslated region), in miRNAs, tRNAs, rRNAs and so on. To avoid any misunderstanding about the width of the applicability, changes that are inconsequential ('silent') from a coding perspective may still alter gene expression of a certain protein as some codons for the same amino acid may be more preferred than others and may lead, for instance, to different transcription stability or translation efficiency, causing the encoded protein to become more or less abundant than without the change.

TABLE 1

| Target codon | Amino acid | Corrected codon | Amino acid |
|---|---|---|---|
| AAG | Lys | GAA | Glu |
|  |  | AGA | Arg |
|  |  | AAG | Lys |
|  |  | GGA | Gly |
|  |  | AGG | Arg |
|  |  | GAG | Glu |
|  |  | GGG | Gly |
| AAG | Asn | GAC | Asp |
|  |  | AGC | Ser |
|  |  | GGC | Gly |
| AAG | Lys | GAG | Glu |
|  |  | AGG | Arg |
|  |  | GGG | Gly |
| AAU | Arg | GAU | Asp |
|  |  | AGU | Ser |
|  |  | GGU | Gly |
| ACA | Thr | GCA | Ala |
|  |  | ACG | Thr |
|  |  | GCG | Ala |
| ACC | Thr | GCC | Ala |
| ACG | Thr | GGG | Ala |
| ACU | Thr | GCU | Ala |
| AGA | Arg | GGA | Gly |
|  |  | AGG | Arg |
|  |  | GGG | Gly |
| AGC | Ser | GGC | Gly |
| AGG | Arg | GGG | Gly |
| AGU | Ser | GGU | Gly |
| AUA | Ile | GAU | Asp |
|  |  | AUG | Met |
|  |  | GUG | Val |
| AUC | Ile | GUC | Val |
| AUG | Met | GUG | Val |
| AUU | Ile | GUU | Val |
| CAA | Gln | CGA | Arg |
|  |  | CAG | Gln |
|  |  | GGG | Arg |
| CAC | His | GGC | Arg |
| CAG | Gln | CGG | Arg |
| CAU | His | CGU | Arg |
| CCA | Pro | CCG | Pro |
| CGA | Arg | CGG | Arg |
| CUA | Leu | CUG | Leu |
| GAA | Glu | GGA | Gly |
|  |  | GAG | Glu |
|  |  | GGG | Gly |
| GCA | Ala | GCG | Ala |
| GUA | Val | GUG | Val |
| GGA | Gly | GGG | Gly |
| GAC | Asp | GGC | Gly |
| GAG | Glu | GGG | Gly |
| GAU | Asp | GGU | Gly |
| UAA | Stop | UGA | Stop |
|  |  | UAG | Stop |
|  |  | UGG | Trp |
| UCA | Ser | UCG | Ser |
| UGA | Stop | UGG | Trp |
| UUA | Leu | UUG | Leu |
| UAC | Tyr | UGC | Cys |
| UAG | Stop | UGG | Trp |
| UAU | Tyr | UGU | Cys |

Particularly interesting target adenosines for editing using oligonucleotides according to the invention are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, protein cleavage by proteases (to mature the protein and/or as part of the intracellular routing), and so forth. Many genetic diseases are caused by G-to-A mutations, and these are preferred target diseases because adenosine deamination at the mutated target adenosine will in principle reverse the mutation to wild-type. However, reversal to wild-type may not always be necessary to obtain a beneficial effect. Modification of an A to a G in a target may also be beneficial if the wild-type nucleotide is other than a G. In certain circumstances this may be predicted to be the case, in others this may require some testing. In certain circumstances, the modification from an A in a target RNA to a G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A-to-G transition brought about by editing in accordance with the invention is in a non-coding RNA, or a non-coding part of an RNA, the consequence may also be inconsequential or less severe than the original mutation. Those of ordinary skill in the art will understand that the applicability of the current invention is very wide and is not even limited to preventing or treating disease. The invention may also be used to modify transcripts to study the effect thereof, even if, or particularly when, such modification induces a diseased state, for example in a cell or a non-human animal model. Preferred examples of genetic diseases that can be prevented and/or treated with oligonucleotides according to the invention are any disease where the modification of one or more adenosines in a target RNA will bring about a (potentially) beneficial change.

Transcribed RNA sequences that are potential target RNA sequences according to the invention, containing mutations of particular interest include, but are not limited to those transcribed from the CFTR gene (the cystic fibrosis transmembrane conductance regulator), dystrophin, huntingtin, neurofibromin 1, neurofibromin 2, the β-globin chain of haemoglobin, CEP290 (centrosomal protein 290 kDa), the HEXA gene of the β-hexosaminidase A, and any one of the Usher genes (e.g. USH2B encoding Usherin) responsible for a form of genetic blindness called Usher syndrome. A more extensive list is presented further below. The target sequence will be selected accordingly, and the oligonucleotide construct will include the desired modification in order to correct the mutation. Those skilled in the art of CF mutations recognise that between 1000 and 2000 mutations are known in the CFTR gene, including R117H, G542X, G551D, R553X, W1282X, and N1303K. In general, mutations in any target RNA that can be reversed using oligonucleotide constructs according to the invention are G-to-A mutations, in the case of adenosine deaminase recruitment, and U-to-C mutations in the case of cytidine deaminase recruitment, and oligonucleotide constructs can be designed accordingly. Mutations that may be targeted using oligonucleotide constructs according to the invention also include C to A, U to A (T to A on the DNA level) in the case of recruiting adenosine deaminases, and A to C and G to C mutations in the case of recruiting cytidine deaminases. Although RNA editing in the latter circumstances may not necessarily revert the mutation to wild-type, the edited nucleotide may give rise to an improvement over the original mutation. For example, a mutation that causes an in-frame stop codon, giving rise to a truncated protein, upon translation, may be changed into a codon coding for an amino acid that may not be the original amino acid in that position, but that gives rise to a (full length) protein with at least some functionality, at least more functionality than the truncated protein. The target sequence is endogenous to the eukaryotic, preferably mammalian, more preferably human cell. Thus the target sequence is preferably not, for instance, a transgene or a marker gene which has been artificially introduced at some point in the cell's history, but rather is a gene that is naturally present in the cell (whether in mutant or non-mutant form). The invention is not limited to correcting mutations, as it may instead be useful to change a wild-type sequence into a mutated sequence by applying oligonucleotides according to the invention. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding, or is involved in secondary structure defining the stability of the mRNA. As noted above, therefore, the invention can be used to provide research tools for diseases, to introduce new mutations which are less deleterious than an existing mutation, etc.

The amount of AON/SON complex to be administered, the dosage and the dosing regimen can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of AON/SON complexes could compete for binding to a nucleic acid editing entity (e.g. ADAR) within a cell, thereby depleting the amount of the entity which is free to take part in RNA editing, but routine dosing trials will reveal any such effects for a given AON/SON complex and a given target of the AON. One suitable trial technique involves delivering the AON/SON complex to cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples.

A method of the invention can thus include a step of identifying the presence of the desired change in the cell's target RNA sequence, thereby verifying that the target RNA sequence has been modified. This step will typically involve sequencing of the relevant part of the target RNA, or a cDNA copy thereof (or a cDNA copy of a splicing product thereof, in case the target RNA is a pre-mRNA), as discussed above, and the sequence change can thus be easily verified. Alternatively the change may be assessed on the level of the protein (length, glycosylation, function or the like), or by some functional read-out, such as a(n) (inducible) current, when the protein encoded by the target RNA sequence is an ion channel, for example. In the case of CFTR function, an Ussing chamber assay or an NPD test in a mammal, including humans, are well known to a person skilled in the art to assess restoration or gain of function.

After RNA editing has occurred in a cell, the modified RNA can become diluted over time, for example due to cell division, limited half-life of the edited RNAs, etc. Thus, in practical therapeutic terms a method of the invention may involve repeated delivery of an AON/SON complex until enough target RNAs have been modified to provide a tangible benefit to the patient and/or to maintain the benefits over time.

AON/SON complexes of the invention are particularly suitable for therapeutic use, and so the invention provides a pharmaceutical composition comprising an AON/SON complex of the invention and a pharmaceutically acceptable carrier. In some embodiments of the invention the pharmaceutically acceptable carrier can simply be a saline solution. This can usefully be isotonic or hypotonic, particularly for pulmonary delivery. The invention also provides a delivery device (e.g. syringe, inhaler, nebuliser) which includes a pharmaceutical composition of the invention.

The invention also provides an AON/SON complex of the invention for use in a method for making a change in a target RNA sequence in a mammalian, preferably human cell, as described herein. Similarly, the invention provides the use of an AON/SON complex of the invention in the manufacture of a medicament for making a change in a target RNA sequence in a mammalian, preferably human cell, as described herein.

The invention also relates to a method for the deamination of at least one specific target adenosine present in a target RNA sequence in a cell, said method comprising the steps of: providing said cell with an AON/SON complex according to the invention; allowing uptake by the cell of said AON (preferably complexed to its complementary SON); allowing annealing of said AON to the target RNA sequence; allowing a mammalian ADAR enzyme comprising a natural dsRNA binding domain as found in the wild type enzyme to deaminate said target adenosine in said target RNA sequence to an inosine; and optionally identifying the presence of said inosine in the RNA sequence. Introduction of the AON (either or not complexed to its complementary SON) according to the present invention into the cell is performed by general methods known to the person skilled in the art. After deamination the read-out of the effect (alteration of the target RNA sequence) can be monitored through different ways. Hence, the identification step of whether the desired deamination of the target adenosine has indeed taken place depends generally on the position of the target adenosine in the target RNA sequence, and the effect that is incurred by the presence of the adenosine (point mutation, early stop codon, aberrant splice site, alternative splice site, misfolding of the resulting protein, etc.). Hence, in a preferred aspect, depending on the ultimate deamination effect of A-to-I conversion, the identification step comprises: sequencing the target RNA; assessing the presence of a functional, elongated, full length and/or wild type protein when said target adenosine is located in a UGA or UAG stop codon, which is edited to a UGG codon through said deamination; assessing the presence of a functional, elongated, full length and/or wild-type protein when two target adenosines are located in a UAA stop codon, which is edited to a UGG codon through the deamination of both target adenosines; assessing whether splicing of the pre-mRNA was altered by said deamination; or using a functional read-out, wherein the target RNA after said deamination encodes a functional, full length, elongated and/or wild type protein. In the event that there is a UAA stop codon it means that both adenosines need to be deaminated. Hence, the invention also relates to AON/SON complexes and methods wherein two adenosines that are next to each other are co-deaminated by an RNA editing enzyme such as ADAR. In this particular case, the UAA stop codon is converted into a UGG Trp-encoding codon (see Table 1). Because the deamination of the adenosine to an inosine may result in a protein that is no longer suffering from the mutated A at the target position, the identification of the deamination into inosine may also be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. When the presence of a target adenosine causes aberrant splicing, the read-out may be the assessment of whether the aberrant splicing is still taking place, or not, or less. On the other hand, when the deamination of a target adenosine is wanted to introduce a splice site, then similar approaches can be used to check whether the required type of splicing is indeed taking place. A very suitable manner to identify the presence of an inosine after deamination of the target adenosine is of course RT-PCR and sequencing, using methods that are well-known to the person skilled in the art, and as outlined herein.

The present invention relates to an AON capable of forming a double stranded complex with a target RNA sequence in a cell, preferably a human cell, for the deamination of a target adenosine in the target RNA sequence by an ADAR enzyme present in the cell, said AON comprising a Central Triplet of 3 sequential nucleotides, wherein the nucleotide directly opposite the target adenosine is the middle nucleotide of the Central Triplet, wherein 1, 2 or 3 nucleotides in said Central Triplet comprise a sugar modification and/or a base modification; with the proviso that the middle nucleotide does not have a 2'-O-alkyl modification, such as a 2'-O-methyl modification, and wherein the AON is complexed to a SON that renders the AON/SON complex more stable; thereby increasing the rate and/or efficiency of ADAR-driven RNA editing through the AON targeting the target sequence. This complexing between AON and SON may not only reduce the vulnerability towards nuclease activity, it may also (perhaps as a result thereof) increase cell penetration and/or intracellular trafficking and finally reaching the target sequence. It is likely that the less breakdown the AON molecules experience, the more AON molecules reach the target and the more efficient RNA editing may occur at the target sequence. The SON as used in the AON/SON complexes of the present invention may either be RNA or DNA or a combination thereof, and is generally complexed to the AON before entry into the cell. The sugar and/or base modification of the nucleotides of the present invention render the AON stable to a certain level and/or cause an improved induction of deamination of the target adenosine as compared to AONs not carrying the sugar and/or base modification. However, because certain nucleotides within the AON, preferably those that are opposite the target adenosine or present within the Central Triplet are not modified to render the AON more stable, the overall stability of the AON is at stake and can be protected by the complex formation with a complementary SON. In a preferred embodiment 2 or 3 nucleotides (in the latter case 3=all nucleotides) within the Central Triplet do not carry a 2'-O-alkyl modification, such as a 2'-O-methyl modification. In a preferred embodiment, the non-complementary nucleotide that is directly opposite the target adenosine when the double stranded complex is formed, is a cytidine. This cytidine, together with the nucleotides that are directly 5' and 3' of it in the AON together form the Central Triplet as defined herein. Although there may be additional mismatches between the AON and the target RNA sequence outside the Central Triplet, the cytidine in the centre of the Central Triplet forms at least one mismatch with the target adenosine in the target sequence such that it can be edited by the ADAR present in the cell. The cell is preferably a human cell and the ADAR is preferably a human ADAR, more preferably an endogenous ADAR in said cell without the need to over-express it by recombinant means. In any event, the middle nucleotide in the Central Triplet does not have a 2'-O-alkyl modification, such as a 2'-O-methyl modification, allowing the cellular RNA editing enzyme(s) to act. In another preferred embodiment, 1 or 2 nucleotides in the Central Triplet other than the middle nucleotide are replaced by an inosine. This may be preferred to allow a better fit with the ADAR enzyme. In yet another preferred embodiment, the AON does not comprise a portion that is capable of forming an intramolecular stem-loop structure that is capable of binding a mammalian ADAR enzyme.

In co-pending applications filed by the same applicant (GB 1614858.7, GB 1616374.3 and GB 1621467.8), the Central Triplet of the AON comprises nucleotides with chemical modifications that improve serum stability. It is to be understood that while the present invention proposes an alternative solution for serum instability, nothing prevents using a combination of the two approaches, i.e. have chemically modified nucleotides in the Central Triplet that are compatible with ADAR editing and a protective SON to further improve stability. Certain chemical modifications in the Central Triplet in fact improve ADAR editing efficiency without necessarily improving serum stability; under these circumstances, complexing such AONs with a protective SON—in accordance with the present invention—would be especially beneficial.

One preferred sugar (modification) in AONs of the present invention is selected from the group consisting of deoxyribose (i.e. DNA), Unlocked Nucleic Acid (UNA) and 2'-fluororibose. In another preferred aspect, the AON comprises at least one internucleoside linkage modification selected from the group consisting of phosphorothioate, 3'-methylenephosphonate (i.e. 3'-O-methylphosphonate internucleotide linkage), 5'-methylenephosphonate (i.e. 5'-O-methylphosphonate internucleotide linkage), 3'-phosphoroamidate (i.e. N-3'-phosphoroamidate internucleotide linkage) and 2'-5'-phosphodiester (i.e. 2'-5'-phosphodiester internucleotide linkage). Especially preferred are phosphorothioate linkages. Further preferred AONs are those wherein the 2, 3, 4, 5, or 6 terminal nucleotides of the 5' and 3' terminus of the AON are linked with phosphorothioate linkages, preferably wherein the terminal 5 nucleotides at the 5' and 3' terminus are linked with phosphorothioate linkages. Preferably, the SONs are modified such that all positions comprise phosphorothioate linkages. SONs are preferably oligoribonucleotides and fully 2'-O-methyl modified.

The AON/SON complex according to the invention is suitably administrated in aqueous solution, e.g. saline, or in suspension, optionally comprising additives, excipients and other ingredients, compatible with pharmaceutical use, at total RNA/DNA concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by inhalation (e.g. through nebulization), intranasally, orally, by injection or infusion, intravenously, subcutaneously, intra-dermally, intra-cranially, intracerebroventricularly, intramuscularly, intra-tracheally, intraperitoneally, intra-rectally, by direct injection into a tumor, and the like. Administration may be in solid form, in the form of a powder, a pill, or in any other form compatible with pharmaceutical use in humans.

The invention is particularly suitable for treating genetic diseases, such as cystic fibrosis, albinism, alpha-1-antitrypsin (A1AT) deficiency, Alzheimer disease, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Hurler Syndrome, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Parkinson's disease, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, various forms of cancer (e.g. BRCA1 and 2 linked breast cancer and ovarian cancer), and the like.

In some embodiments the AON/SON complex can be delivered systemically, but it is more typical to deliver an AON/SON complex to cells in tissues in which the target sequence's phenotype is seen. For instance, mutations in CFTR cause cystic fibrosis which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI eFlow (Rapid) or the i-neb from Respironics. Inhaled use of oligonucleotide constructs can lead to systemic distribution of the oligonucleotide construct and uptake by cells in the gut, liver, pancreas, kidney and salivary gland tissues, among others. It is therefore to be expected that inhaled delivery of AON/SON complexes according to the invention can also target these cells efficiently, which in the case of CFTR gene targeting could lead to amelioration of gastrointestinal symptoms also associated with cystic fibrosis. For other target sequences, depending on the disease and/or the target organ, administration may be topical (e.g. on the skin), intradermal, subcutaneous, intramuscular, intravenous, oral, ocular injection, etc. In some diseases the mucus layer shows an increased thickness, leading to a decreased absorption of medicines via the lung. One such a disease is chronical bronchitis, another example is cystic fibrosis. Various forms of mucus normalizers are available, such as DNAses, hypertonic saline or mannitol, which is commercially available under the name of Bronchitol. When mucus normalizers are used in combination with RNA editing oligonucleotide constructs, such as the AON/SON complexes according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the AON/SON complexes according to the invention can be combined with administration of small molecule for treatment of CF, such as potentiator compounds for example Kalydeco (ivacaftor; VX-770), or corrector compounds, for example VX-809 (lumacaftor) and/or VX-661. Other combination therapies in CF may comprise the use of an AON/SON complex according to the invention in combination with an inducer of adenosine deaminase, using IFN-gamma or TNF-alpha. Alternatively, or in combination with the mucus normalizers, delivery in mucus penetrating particles or nanoparticles can be applied for efficient delivery of RNA editing molecules to epithelial cells of for example lung and intestine. Accordingly, administration of an AON/SON complex according to the invention to a subject, preferably a human subject, preferably uses delivery in mucus penetrating particles or nanoparticles. Chronic and acute lung infections are often present in patients with diseases such as cystic fibrosis. Antibiotic treatments reduce bacterial infections and the symptoms of those such as mucus thickening and/or biofilm formation. The use of antibiotics in combination with AON/SON complexes according to the invention could increase effectiveness of the RNA editing due to easier access of the target cells for the AON (either or not complexed to the SON). Accordingly, administration of an AON/SON complex according to the invention to a subject, preferably a human subject, is preferably combined with antibiotic treatment to reduce bacterial infections and the symptoms of those such as mucus thickening and/or biofilm formation. The antibiotics can be administered systemically or locally or both.

EXAMPLES

Example 1. Protection of an RNA-Editing Inducing AON by Annealing it to a Sense Oligonucleotide ADAR59-2 was selected as an exemplary antisense oligonucleotide. This AON had previously been shown to efficiently harness endogenous ADARs to induce site-specific RNA editing (GB 1610923.3 and GB 1614669.8; both unpublished), but also to suffer from degradation upon incubation with cell culture medium. The 3' to 5' sequence of ADAR59-2 is shown in FIG. 1. The editing target is a green fluorescent protein (GFP) mutant W57X, wherein editing a mutated adenosine into an inosine restores an open reading frame and leads to a full-length protein (inosine is interpreted by cellular machineries as guanosine). See WO 2016/097212 for details of the pGFPstop57 plasmid encoding the mutant GFP.

First, 0.8 µg of plasmid pGFPstop57 was transfected with Lipofectamine 2000 into MCF-7 cells (0.32*10$^6$ cells in 2 ml of DMEM supplemented with 10% FBS) that express endogenous ADAR proteins. 24 hours later, ADAR59-2 was annealed with nine different SONs (FIG. 1) in annealing buffer (10 mM Tris-HCl, pH 7.5, 50 mM KCl, 0.5 mM EDTA) by heating up to 95° C. for three minutes, and then slowly cooling down to 20° C. over the course of 50 min. The resulting complexes were transfected into the same cells with Lipofectamine 2000, at a final concentration of 100 nM AON-SON complex. Simultaneously, aliquots of the annealed complexes and SONs as such were incubated for 30 min at 37° C. either with phosphate buffered saline (PBS) or cell culture medium supplemented with 15% fetal bovine serum (FBS). The stabilities of these samples were then analysed by denaturing Urea-polyacrylamide gel electrophoresis (PAGE). 48 hours after the second transfection the cells were collected, total RNA extracted and subjected to RT-PCR, and the PCR products were analysed by Sanger sequencing in order to detect A-to-I (A-to-G) editing. The sequences and chemical modifications present in ADAR59-2 and in the nine SONs are detailed in FIG. 1.

FIG. 2 shows the results of the stability assays. ADAR59-2 and the SONs were maintained in PBS (noted as CTL) or in cell culture medium with 15% FBS (noted as RX). It was noted that ADAR59-2 and most of the SONs appeared quite unstable in FBS-supplemented medium as such. In contrast thereto, the complexes of ADAR59-2+any of the SONs display high stability that withstands even denaturing conditions in the gel. GFP-SON-9 cannot be analysed by denaturing PAGE because the lack of negative charge in the backbone prevents it from entering the gel. However, the complex between ADAR59-2 and GFP-SON-9 is very stable in the experimental conditions. The DNA-oligonucleotides SON-7 and SON-8 are very stable without being bound to a complementary strand (FIG. 2, upper right panel).

A few examples of sequencing results surrounding the editing site within the GFP-mRNA are shown in FIG. 3. The edited adenosine is marked with an arrow and the size of the black guanosine peak over the adenosine peak indicates successful editing. A-to-I editing as compared to ADAR59-2 alone was significantly increased, especially in AON/SON complexes using GFP-SON-4, -5 and -6.

Example 2. RNA Editing Using AON/SON Complexes in SNU-475 Cells

The experiment of example 1 was repeated with SNU-475 cells that were transfected with 25 ng GFPstop57 plasmid and subsequently transfected with AON59-2 alone or AON59-2 protected by SON-6 in amounts as indicated in the example above. Sequencing results (depicted in FIG. 4) show that the rate of RNA editing found with AON59-2 alone is significantly increased when the oligonucleotide is pre-incubated and protected by SON-6.

It was shown that RNA editing inducing AONs become more effective in editing when complexed to small, complementary SONs. The exact mechanism of action of these complexes remains to be elucidated. It is likely that the increased double-stranded character of the molecule is more effective in resisting degradation by nucleases, but the complex may also increase cellular uptake, may enhance the release from endosomes, or affect ADAR binding/activity. Whatever the exact mechanism, SONs with phosphorothioate and 2'-O-methyl modifications appeared most effective in reducing nuclease activity and most effective in increasing AON-dependent RNA editing efficiency.

Example 3. RNA Editing with AON/SON Complexes in HEPA1-6 & CMT64 Cells on Small Nuclear Ribonucleoprotein Polypeptide A (SNRPA) mRNA It was investigated whether it was possible to achieve RNA editing in vitro with endogenous ADAR proteins. Small Nuclear Ribonucleoprotein Polypeptide A (SNRPA) was chosen as an endogenous target due to its medium abundant and ubiquitous expression. SNRPA associates with stem loop II of the U1 small nuclear ribonucleoprotein, which binds the 5' splice site of precursor mRNAs and is required for splicing. The protein auto-regulates itself by polyadenylation inhibition of its own pre-mRNA via dimerization and has been implicated in the coupling of splicing and polyadenylation. Antisense oligonucleotides (AONs) were designed to edit the wild type stop codon (UAG) of mouse SNRPA which would then likely lead to extension of the mRNA and resulting in a larger protein with an increase of 25 amino acids encoded by the downstream sequences. The original size of the SNRPA protein is approximately 31.68 kDa and the enlarged protein is calculated to be around 34.43 kDa. The AON that was used for this purpose was ADAR94-1: 5'-g*a*c*u*gagguacuccuuagagaaaggugCCAcuucuuggcaa*a*g*g*a-3' (SEQ ID NO: 14). Lower case nucleotides are RNA and 2'-O-methyl modified. Upper case is DNA and is the Central Triplet with the middle C being opposite the target adenosine. The asterisks refer to phosphorothioate linkages.

Figure 5A:
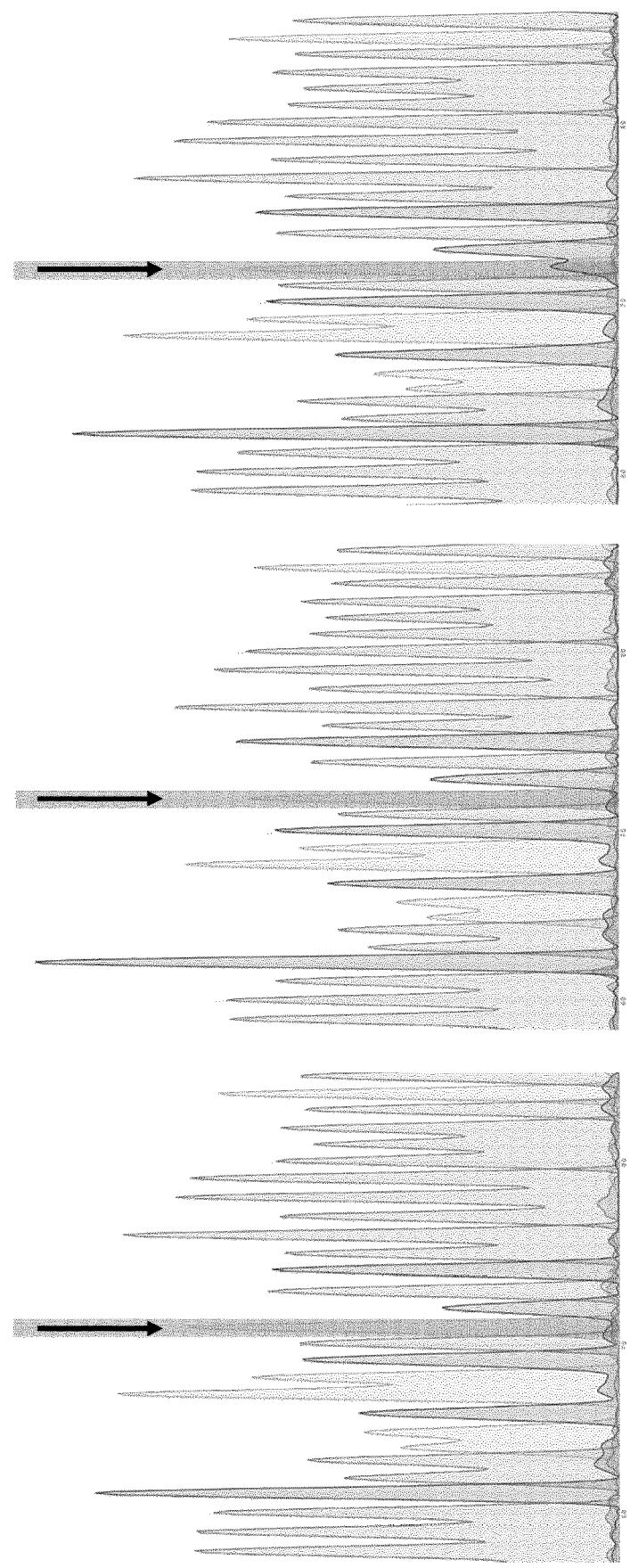
FIG. 5 shows the sequencing results of a PCR product generated via cDNA from RNA isolated from mouse HEPA1-6 cells (A) and CMT64 cells (B) that were either not-transfected (NT, left panels) or transfected with a non-targeting control oligonucleotide (NTO, middle panels) or with ADAR94-1 (right panels) in combination with a SON to edit the stop codon of the mouse SNRPA mRNA. RNA editing that is clearly above background levels is observed at the position indicated by the arrow. The sequence represented by the peaks in each of the three figures is 5'-TTTGC-CAAGAAGTAGCGCCTTTCCCTAT-3' (SEQ ID NO: 11), with the target adenosine underlined.
Figure 6:
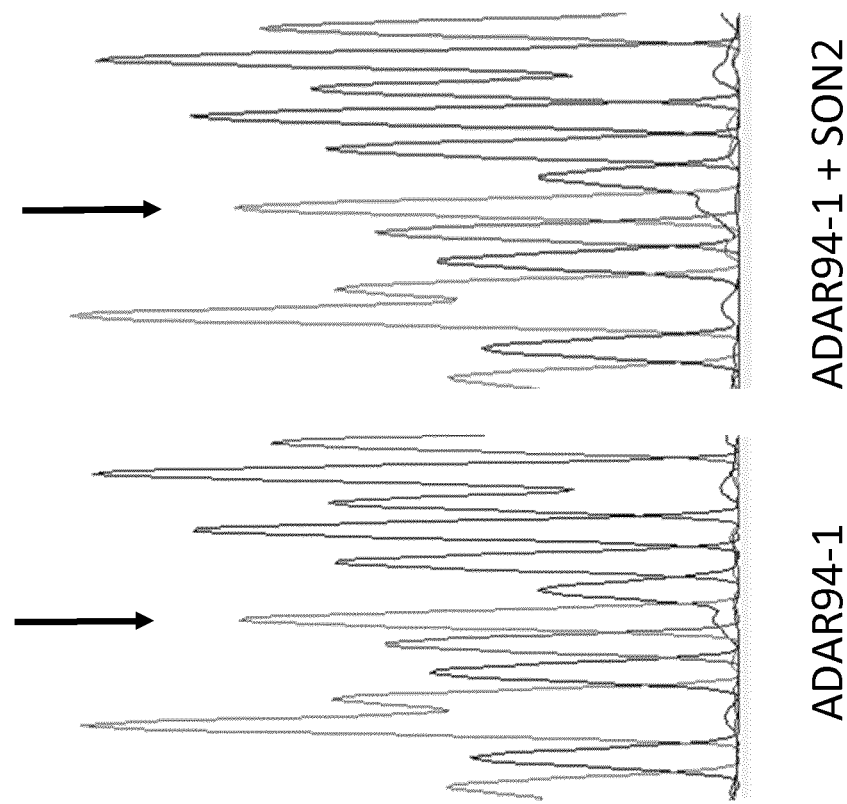
FIG. 6 shows the sequencing results of a PCR product generated via cDNA from RNA isolated from mouse HEPA1-6 cells that were transfected with ADAR94-1 alone or ADAR94-1 in combination with SON2 as described in FIG. 5. The sequence represented by the peaks in each of the two figures is 5'-AGAAGTAGCGCCT-3' (SEQ ID NO: 12), with the target adenosine underlined and indicated by the arrow.

ADAR94-1 was tested in HEPA1-6 and CMT-64 cell lines. HEPA1-6 is derived from a BW7756 mouse hepatoma that arose in a C57/L mouse. CMT-64 was isolated from a primary alveogenic lung carcinoma tumor mass in C57BL/1crf mouse. Cells were plated in a 6-well plate 24 h prior to transfection in a density of $1.75 \times 10^5$ cells/well for HEPA1-6, and $1.5 \times 10^5$ cells/well for CMT-64. Both cell lines were cultured in regular culture medium (DMEM+10% FBS). Cells were either not transfected (NT control), transfected with an unrelated non-targeting oligo (NTO control; 200 nM of a 50-mer oligonucleotide) or transfected with final concentration of 100 nM ADAR94-1 plus a mouse specific Snrpa-related sense oligonucleotide that is thought to stabilize the AON (SON2: 5'-a*a*g*a*A*G*U*G*G*C*A*c*c*u*u-3' (SEQ ID NO: 15); lower and upper case is here both RNA but lower case represents RNA nucleotides that are 2'-O-methyl modified; the asterisks represent phosphorothiate linkages). AON and SON were diluted to 100 µM stocks and mixed to a 1:1 ratio and incubated with the following annealing program: 60° C. 5 min, 55° C. 5 min, 50° C. 5 min, 45° C. 5 min, 40° C. 5 min, 35° C. 5 min, 30° C. 5 min, 20° C. 5 min, 10° C. until use. Transfections were performed using Lipofectamine 2000 (Invitrogen) following the manufacturers protocol. Prior to transfection, medium was replaced to 1.7 mL/well fresh medium and transfection mix (300 µl) was added, making a total of 2 mL/well. 24 h after transfection 2 mL fresh medium was added to each well. Cells were incubated for another 24 h. Then, medium was removed and cells were washed once with 1×PBS and then 350 µl Trizol was added to each well for cell lysis. The lyzed cells were then collected and RNA was extracted with the Direct-Zol RNA miniprep (Zymo) following the instructions provided by the manufacturer. It was chosen not to use the on-column DNAse of this kit, but instead the TURBO DNA-free™ Kit for DNAse treatment of the RNA samples. For this 0.5 µl of RNAse inhibitor was added to each sample, and the rest of the steps were performed according to the manufacturer instructions. RNA concentrations were measured using the Nanodrop and 400 ng RNA was used for cDNA synthesis with the Maxima Reverse Transcriptase kit (ThermoFisher Scientific) using the protocols of the manufacturer. PCR was performed using forward primer Fw1_mSNRPA (5'-GCCTTCGTGGAGTTTGACA-3'; SEQ ID NO: 16) and reverse primer Rev1_mSNRPA (5'-ACACACGGCTCT-GAGAAGGT-3'; SEQ ID NO: 17) using methods generally known to the person skilled in the art. PCR products were checked on an Agilent 2100 Bioanalyzer and purified with the Nucleo-Spin Gel and PCR clean-up kit (Macherey-Nagel). Purified products were sequenced with the sequencing primer Snrp-1-Fw1 (5'-CGTGGAGTTTGACAAT-GAAGT-3'; SEQ ID NO: 18). Sequencing results for the HEPA1-6 cells are shown in FIG. 5A and the sequencing results for the CMT64 cells are shown in FIG. 5B. Clearly, the non-transfected (NT, left panels) and non-targeting control oligonucleotide (NTO, middle panels) control show no detectable RNA editing at the stop codon (middle position of the stop codon indicated by an arrow). However, as can be clearly seen in the right panels, there is significant RNA editing detectable when the ADAR94-1 oligonucleotide was used (here in combination with the protecting SON2 oligonucleotide), both in HEPA1-6 cells as in CMT64 cells. To investigate the effect of the annealing SON, the same experiment was performed with and without SON2. FIG. 6 shows that this SNRPA RNA editing can also be achieved without the protecting SON, but that the addition of the SON clearly boosts the level of editing. Procedures for this +/−SON experiment were similar to that described above and performed in HEPA1-6 cells. This shows that RNA editing can be achieved with endogenous ADAR using endogenous SNRPA target RNA as a model, and that the addition of a protecting SON to the targeting AON further increases such RNA editing.

Figure 7:
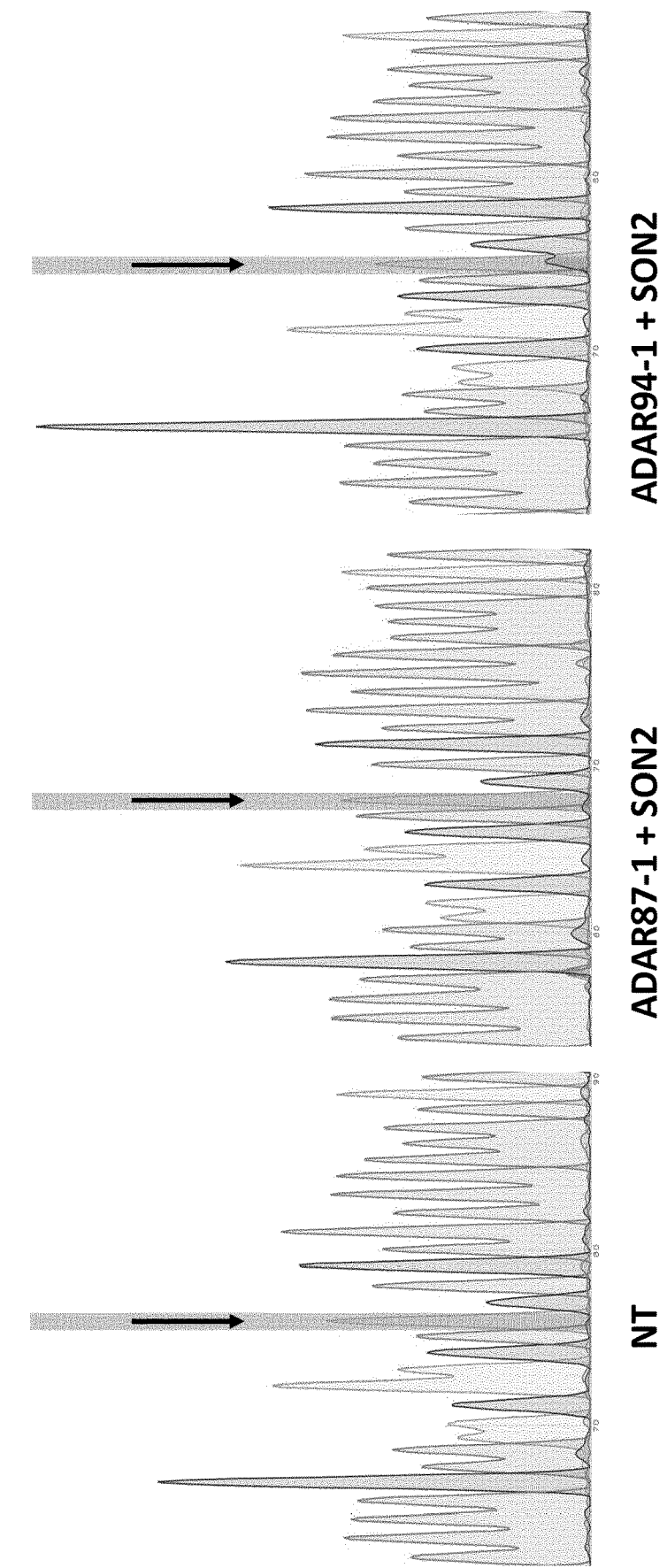
FIG. 7 shows the sequencing results of a PCR product generated via cDNA from RNA isolated from primary mouse lung cells that were either not transfected (NT, left panel), transfected with (middle panel) a control oligonucleotide (ADAR87-1) annealed to a protecting sense oligonucleotide (SON2), or (right panel) with an oligonucleotide targeting the mouse SNRPA RNA (ADAR94-1) annealed to SON2. A clear increase in G signal is seen after transfection with ADAR94-1+SON2 (right panel, indicated by an arrow), which shows that highly specific and significant RNA editing can be achieved with endogenous ADAR on an endogenous target in ex vivo primary cells. The sequence represented by the peaks in each of the three figures is 5'-TTTTGCCAAGAAGT<u>A</u>GCGCCTTTCCCTAT-3' (SEQ ID NO: 13), with the target adenosine underlined and indicated by the arrow.

Example 4. RNA Editing Using AON/SON Complexes in Murine WT Primary Lung Cells on Small Nuclear Ribonucleoprotein Polypeptide A (SNRPA) mRNA After having found evidence of in vitro ADAR-mediated RNA editing of the Snrpa target sequence as described in example 3, it was investigated whether it was possible to achieve RNA editing ex vivo with endogenous ADAR proteins in murine wild type primary lung cells using the same ADAR94-1 oligonucleotide in the context of SON2. Cells were isolated from a mouse with a C57BL/6J background using a mouse lung dissociation kit from Miltenyi Biotec (Article nr. 130-095-927). In short, all reagents were prepared under sterile conditions according to the manufacturer. Mice were sacrificed by $CO_2$ asphyxiation and perfused with PBS. Mouse lungs were then dissected from the body and transferred to a 50 ml tube containing PBS on ice. Mouse lungs were subsequently dissected into single lobes and transferred to a gentleMACS C-tube containing a kit-specific enzyme mix. Tissue was processed using the gentleMACS program 37C_m_LDK_1. After termination of the program, samples were applied to a MACS SmartStrainer (70 µm) and centrifuged at 300×g for 10 min at 4° C. Supernatant was discarded and cells were resuspended in 10 ml DMEM+10% FBS, counted and cultured in an appropriate culture flask until further processing. For transfection, cells were plated at a density of $3.0 \times 10^5$ cells/well. The AONs were annealed to SON2 as described in example 3. Cells were either not transfected (NT), transfected with final concentration of 100 nM AON/SON complex targeting the human Snrpa sequence (ADAR87-1+SON2) or transfected with final concentration of 100 nM AON/SON complex targeting the mouse Snrpa sequence (ADAR94-1+SON2) using Turbofect (ThermoFisher Scientific) following the manufacturer's protocol. 6 h after transfection, the medium was replaced with fresh DMEM+10% FBS and cells were cultured in total for 48 h after transfection. After these 48 h, cells were washed once with 1×PBS and 350 µl Trizol was added to each well for cell lysis. RNA was extracted with the Direct-Zol RNA miniprep (Zymo) according to the manufacturer's protocol. RNA concentrations were measured using the Nanodrop and 500 ng RNA was used for cDNA synthesis with the Maxima Reverse Transcriptase kit (ThermoFisher Scientific) according to the manufacturer's protocol. PCR was performed using forward primer Fw2_mSNRPA (5'-GCTCTCCATGCTCTTCAACC-3'; SEQ ID NO: 19) and reverse primer Rev2_mSNRPA (5'-TCAGGGACTGAGCCAAGG-3'; SEQ ID NO: 20) using methods generally known to the person skilled in the art. PCR products were checked on an Agilent 2100 Bioanalyzer and purified with the Nucleo-Spin Gel and PCR clean-up kit (Macherey-Nagel). Purified products were sequenced with sequencing primer Snrp-1-Fw1. Sequencing results are shown in FIG. 7. The targeted A in the TAG stop codon is depicted by an arrow. ADAR mediated editing will be visible in DNA sequences as a G peak under the A peak in the TAG codon. The non-transfected (NT) and non-targeting control complex (ADAR87-1+SON2) show no detectable RNA editing at the TAG stop codon. However, when cells are transfected with ADAR94-1+SON2 complex a clear detectable editing is observed in the TAG stop codon. The conclusion is that RNA editing can be achieved with endogenous ADAR using SNRPA target RNA as a model. Moreover, as the cells used in this example are directly isolated from mice, this indicates that site-specific RNA editing with endogenous ADAR on an endogenous target using a (therapeutic) AON/SON complex is feasible in vivo.

The invention claimed is:

1. A double stranded oligonucleotide complex comprising an ADAR-recruiting antisense oligonucleotide (AON) and a complementary sense oligonucleotide (SON) annealed to the AON via Watson-Crick base-pairing, wherein (i) the AON is capable of forming a double stranded complex with a target RNA sequence in a cell for the deamination of a target adenosine in the target RNA sequence by an ADAR enzyme present in the cell, (ii) the AON comprises a Central Triplet of three sequential nucleotides, (iii) the nucleotide directly opposite the target adenosine is the middle nucleotide in the Central Triplet, (iv) 1, 2 or 3 nucleotides in the Central Triplet comprise a sugar modification and/or a base modification, (v) the middle nucleotide does not have a 2'-O-alkyl modification, and (vi) the middle nucleotide is a cytidine.

2. The double stranded oligonucleotide complex of claim 1, wherein the AON comprises at least one nucleotide that is sensitive to nuclease dependent degradation, and wherein the SON is complementary to the at least one nucleotide that is sensitive to nuclease dependent degradation.

3. The double stranded oligonucleotide complex of claim 2, wherein the SON is complementary to all nucleotides in the AON that are sensitive to nuclease dependent degradation.

4. The double stranded oligonucleotide complex of claim 1, wherein the SON comprises a chemical modification assisting in improving a pharmacokinetic and/or a pharmacodynamics property of the complex, wherein the property is selected from the group consisting of: nuclease stability, cellular uptake, intracellular trafficking, and ADAR-mediated AON-guided editing of a target RNA in a cell comprising ADAR.

5. The double stranded oligonucleotide complex of claim 1, wherein the SON comprises a backbone with one or more phosphorothioate internucleosidic linkages and/or one or more 2'-OMe modified riboses.

6. The double stranded oligonucleotide complex of claim 1, wherein the SON is equally long as, or shorter than the AON.

7. The double stranded oligonucleotide complex of claim 1, wherein the SON is fully complementary to the AON.

8. The double stranded oligonucleotide complex of claim 1, wherein the SON comprises one or more mismatches or wobbles when annealed to the AON.

9. The double stranded oligonucleotide complex of claim 1, wherein the SON comprises one or more nucleotides which are RNA, DNA, LNA or BNA or combinations thereof.

10. The double stranded oligonucleotide complex of claim 1, wherein the AON comprises at least one sugar modification selected from the group consisting of deoxyribose (DNA), Unlocked Nucleic Acid (UNA) and 2'-fluororibose.

11. The double stranded oligonucleotide complex of claim 1, wherein the SON comprises only RNA nucleotides.

12. A pharmaceutical composition comprising the double stranded oligonucleotide complex of claim 1, and a pharmaceutically acceptable carrier.

13. A method of treating a disease in a subject in need thereof by ADAR-mediated targeted deamination of a target adenosine in a target RNA sequence in a cell by an ADAR enzyme present in the cell, the method comprising administering to the subject the double stranded oligonucleotide complex of claim 1.

14. The method of claim 13, wherein: (i) the double stranded oligonucleotide complex is provided to a cell comprising at least one specific target adenosine present in a target RNA sequence, (ii) the AON is taken up by the cell, (iii) the AON anneals to the target sequence, and (iv) an ADAR enzyme present in the cell deaminates the target adenosine in the target RNA sequence to an inosine.

15. The method of claim 13, wherein the disease is a genetic disorder selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

16. A method for the deamination of at least one specific target adenosine present in a target RNA sequence in a cell, the method comprising the steps of:
（i) providing the cell with the double stranded oligonucleotide complex of claim 1;
(ii) allowing uptake by the cell of the AON;
(iii) allowing annealing of the AON to the target RNA sequence; and
(iv) allowing an ADAR enzyme present in the cell to deaminate the target adenosine in the target RNA sequence to an inosine; and
(v) optionally identifying the presence of the inosine in the RNA sequence.

17. The method of claim 16, wherein step (v) comprises:
(a) sequencing the target RNA sequence;
(b) assessing the presence of a functional, elongated, full length and/or wild type protein when the target adenosine is located in a UGA or UAG stop codon, which is edited to a UGG codon through the deamination;
(c) assessing the presence of a functional, elongated, full length and/or wild type protein when two target adenosines are located in a UAA stop codon, which is edited to a UGG codon through the deamination of both target adenosines;
(d) assessing whether splicing of the pre-mRNA was altered by the deamination; or
(e) using a functional read-out, wherein the target RNA after the deamination encodes a functional, full length, elongated and/or wild type protein.

18. The method of claim 13, wherein the target RNA sequence encodes CFTR, CEP290, alpha1-antitrypsin (A1AT), Guanine Nucleotide Binding Protein (GNAQ), or LRRK2, or wherein the target RNA is encoded by the IDUA gene.

19. The double stranded oligonucleotide complex of claim 9, wherein the RNA, DNA, LNA or BNA nucleotides are chemically modified in the backbone.

20. The double stranded oligonucleotide complex of claim 11, wherein the RNA nucleotides are chemically modified in the backbone.

* * * * *

UNITED STATES PATENT AND TRADEMARK OFFICE
CERTIFICATE OF CORRECTION

PATENT NO. : 11,274,300 B2
APPLICATION NO. : 16/479101
DATED : March 15, 2022
INVENTOR(S) : A. Aalto et al.

It is certified that error appears in the above-identified patent and that said Letters Patent is hereby corrected as shown below:

In the Specification

In Column 4, Line 63, please replace "Epidermylosis bullosa" with --Epidermolysis bullosa--, therefor.
In Column 4, Lines 64-65, please replace "Familial Adenomatous, Polyposis" with --Familial Adenomatous Polyposis--, therefor.
In Column 4, Lines 65-66, please replace "Glucose-6-phosphate dehydrogenase" with --Glucose-6-phosphate dehydrogenase deficiency--, therefor.
In Column 4, Lines 66-67, please replace "Hereditary Hematochromatosis" with --Hereditary Hemochromatosis--, therefor.
In Column 13, Lines 27-28, please replace "Epidermylosis bullosa" with --Epidermolysis bullosa--, therefor.
In Column 13, Line 29, please replace "Familial Adenomatous, Polyposis" with --Familial Adenomatous Polyposis--, therefor.
In Column 13, Lines 30-31, please replace "Glucose-6-phosphate dehydrogenase" with --Glucose-6-phosphate dehydrogenase deficiency--, therefor.
In Column 13, Lines 31-32, please replace "Hereditary Hematochromatosis" with --Hereditary Hemochromatosis--, therefor.
In Column 13, Line 58, please replace "Epidermylosis bullosa" with --Epidermolysis bullosa--, therefor.
In Column 13, Lines 59-60, please replace "Familial Adenomatous, Polyposis" with --Familial Adenomatous Polyposis--, therefor.
In Column 13, Line 61, please replace "Glucose-6-phosphate dehydrogenase" with --Glucose-6-phosphate dehydrogenase deficiency--, therefor.
In Column 13, Lines 61-62, please replace "Hereditary Hematochromatosis" with --Hereditary Hemochromatosis--, therefor.
In Column 25, Line 2, please replace "Epidermylosis bullosa" with --Epidermolysis bullosa--, therefor.
In Column 25, Lines 3-4, please replace "Familial Adenomatous, Polyposis" with --Familial Adenomatous Polyposis--, therefor.

Signed and Sealed this
Fourth Day of April, 2023

Katherine Kelly Vidal
*Director of the United States Patent and Trademark Office*

CERTIFICATE OF CORRECTION (continued)
U.S. Pat. No. 11,274,300 B2

In Column 25, Line 5, please replace "Glucose-6-phosphate dehydrogenase" with --Glucose-6-phosphate dehydrogenase deficiency--, therefor.
In Column 25, Lines 5-6, please replace "Hereditary Hematochromatosis" with --Hereditary Hemochromatosis--, therefor.

In the Claims

In Column 37, Claim 15, Lines 39-40, please replace "Epidermylosis bullosa" with --Epidermolysis bullosa--, therefor.
In Column 37, Claim 15, Line 41, please replace "Familial Adenomatous, Polyposis" with --Familial Adenomatous Polyposis--, therefor.
In Column 37, Claim 15, Lines 42-43, please replace "Glucose-6-phosphate dehydrogenase" with --Glucose-6-phosphate dehydrogenase deficiency--, therefor.
In Column 37, Claim 15, Lines 43-44, please replace "Hereditary Hematochromatosis" with --Hereditary Hemochromatosis--, therefor.